(12) United States Patent
Marsh et al.

(10) Patent No.: US 12,383,680 B2
(45) Date of Patent: Aug. 12, 2025

(54) ELECTRONIC SYSTEM AND METHOD FOR DETERMINING FAILURE OF A SECOND SWITCH IN A DRUG DELIVERY DEVICE

(71) Applicant: Sanofi, Paris (FR)

(72) Inventors: William Geoffrey Arthur Marsh, Balsall Common (GB); Richard Paul Gledhill, Warwick (GB); Anthony Paul Morris, Balsall Common (GB); Robert Frederick Veasey, Warwickshire (GB); Aidan Michael O'Hare, Coventry (GB); Daniel Paul Jenkins, St. Albens (GB)

(73) Assignee: Sanofi, Paris (FR)

( * ) Notice: Subject to any disclaimer, the term of this patent is extended or adjusted under 35 U.S.C. 154(b) by 838 days.

(21) Appl. No.: 17/574,195

(22) Filed: Jan. 12, 2022

(65) Prior Publication Data
US 2022/0134011 A1 May 5, 2022

Related U.S. Application Data

(63) Continuation-in-part of application No. PCT/EP2021/057669, filed on Mar. 25, 2021.

(30) Foreign Application Priority Data

Mar. 27, 2020 (EP) .................................. 20315066
Jun. 18, 2020 (EP) .................................. 20315305
(Continued)

(51) Int. Cl.
*A61M 5/315* (2006.01)
*A61M 5/20* (2006.01)
(Continued)

(52) U.S. Cl.
CPC .......... *A61M 5/31551* (2013.01); *A61M 5/20* (2013.01); *A61M 5/2033* (2013.01);
(Continued)

(58) Field of Classification Search
CPC ...... A61M 2005/3126; A61M 2205/18; A61M 2205/35; A61M 2205/3561;
(Continued)

(56) References Cited

U.S. PATENT DOCUMENTS 4,908,017 A * 3/1990 Howson .............. A61M 5/1452
604/154
6,663,602 B2 12/2003 Moller
(Continued)

FOREIGN PATENT DOCUMENTS

EP 2729202 5/2018
EP 2890435 3/2020
(Continued)

OTHER PUBLICATIONS

International Search Report and Written Opinion in International Appln. No. PCT/EP2021/057669, dated Jun. 4, 2021, 10 pages.

*Primary Examiner* — Jason E Flick
*Assistant Examiner* — Isabella S North
(74) *Attorney, Agent, or Firm* — Bond, Schoeneck & King, PLLC

(57) ABSTRACT

An electronic system for a drug delivery device comprising a dose setting and drive mechanism with a first member, wherein the first member performs a specific movement relative to a second member during a dose delivery operation. The electronic system comprises a first switch configured to be activated by a pre-defined user operation, wherein the pre-defined user operation includes a user operation that is expected in conjunction with dose delivery operation, a second switch for indicating the specific movement, and a
(Continued)

sensor arrangement for a motion sensor system for providing position data that allows to distinguish between different positions of the first member relative to the second member.

20 Claims, 9 Drawing Sheets

(30) Foreign Application Priority Data

| Jul. 23, 2020 | (EP) | .................................... 20315357 |
| Nov. 16, 2020 | (EP) | .................................... 20315451 |
| May 20, 2021 | (EP) | .................................... 21315085 |

(51) Int. Cl.
*A61M 5/24* (2006.01)
*A61M 5/31* (2006.01)

(52) U.S. Cl.
CPC .......... *A61M 5/24* (2013.01); *A61M 5/31533* (2013.01); *A61M 5/31568* (2013.01); *A61M 2005/3126* (2013.01); *A61M 2205/18* (2013.01); *A61M 2205/33* (2013.01); *A61M 2205/35* (2013.01); *A61M 2205/3561* (2013.01); *A61M 2205/3584* (2013.01); *A61M 2205/502* (2013.01); *A61M 2205/52* (2013.01)

(58) Field of Classification Search
CPC .... A61M 2205/3584; A61M 2205/502; A61M 2205/52; A61M 5/2033; A61M 5/24; A61M 5/31551; A61M 5/31568; A61M 2005/3125; A61M 2205/183; A61M 2205/186; A61M 2205/3592; A61M 2205/3576; A61M 5/2422; A61M 5/3155; A61M 5/31553; A61M 2205/581; A61M 5/31585; A61M 5/31593; A61M 2205/3306; A61M 2205/3327; G16H 20/00; G16H 20/10; G16H 20/17; G08B 21/187; H02K 2213/06
USPC ................. 604/211, 207, 208, 224; 222/390; 324/207.25
See application file for complete search history.

(56) References Cited

U.S. PATENT DOCUMENTS

| 2009/0090188 | A1* | 4/2009 | Saied ...................... G01L 7/084 |
| | | | 73/715 |
| 2013/0184676 | A1* | 7/2013 | Kamen ............... A61M 5/1458 |
| | | | 604/152 |
| 2014/0107579 | A1* | 4/2014 | Lanigan ................ A61M 39/10 |
| | | | 604/151 |
| 2014/0194825 | A1* | 7/2014 | Nielsen ............. A61M 5/31535 |
| | | | 604/207 |
| 2015/0303851 | A1* | 10/2015 | Day ................... A61M 5/14212 |
| | | | 318/696 |
| 2016/0015903 | A1 | 1/2016 | Madsen et al. |
| 2016/0045662 | A1* | 2/2016 | Jakobsen ................ A61M 5/20 |
| | | | 604/207 |
| 2016/0144141 | A1* | 5/2016 | Biswas ............... A61M 15/009 |
| | | | 128/200.23 |
| 2016/0287807 | A1* | 10/2016 | Madsen ............ A61M 5/31551 |
| 2017/0209630 | A1* | 7/2017 | Klusmann ............ A61M 1/984 |
| 2019/0269858 | A1* | 9/2019 | Reich ................ A61M 5/31585 |
| 2019/0373679 | A1* | 12/2019 | Fu ............................ A24F 40/40 |
| 2020/0360614 | A1* | 11/2020 | Schabbach .............. A61M 5/24 |

FOREIGN PATENT DOCUMENTS

| EP | 20315066.9 | 3/2020 | |
| EP | 20315305.1 | 6/2020 | |
| EP | 20315357.2 | 7/2020 | |
| EP | 20315451.3 | 11/2020 | |
| WO | WO 2004/078239 | 9/2004 | |
| WO | WO 2005/018721 | 3/2005 | |
| WO | WO-2018160425 A1 * | 9/2018 | ............. A61M 5/20 |
| WO | WO 2019/040313 | 2/2019 | |
| WO | WO 2019/101962 | 5/2019 | |
| WO | 2020176319 A1 | 9/2020 | |
| WO | WO 2021/191322 | 9/2021 | |
| WO | WO 2021/191325 | 9/2021 | |
| WO | WO 2021/191326 | 9/2021 | |
| WO | WO 2021/191327 | 9/2021 | |

* cited by examiner

ELECTRONIC SYSTEM AND METHOD FOR DETERMINING FAILURE OF A SECOND SWITCH IN A DRUG DELIVERY DEVICE

CROSS REFERENCE TO RELATED APPLICATIONS

The present application claims priority to European Patent Application No. EP21315085.7, filed on May 20, 2021. The present application is also a continuation-in-part of International Patent Application No. PCT/EP2021/057669, filed on Mar. 25, 2021, which claims priority to European Application Nos. EP20315066.9, filed on Mar. 27, 2020; EP20315305.1, filed on Jun. 18, 2020; EP20315357.2, filed on Jul. 23, 2020; and EP20315451.3, filed on Nov. 16, 2020. All disclosures are incorporated herein by reference.

TECHNICAL FIELD

The present invention relates to an electronic system for a drug delivery device comprising a dose setting and drive mechanism with a first member, the electronic system comprising first switch, a second switch indicating a specific movement of the first member relative to a second member, and an additional motion sensor system operable to provide position data that allows to distinguish between different positions of the first member relative to the second member. The present invention further relates to a button module comprising the electronic system, a drug delivery device comprising the electronic system or the button module with the electronic system, and to methods for operating the electronic system.

BACKGROUND

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. The present invention is applicable for disposable and reusable devices.

For such devices the functionality of recording doses that are dialled and delivered from the pen may be of value to a wide variety of device users as a memory aid or to support detailed logging of dose history. Thus, drug delivery devices using electronics are becoming increasingly popular in the pharmaceutical industry as well as for users or patients. For example, a drug delivery device is known from EP 2 729 202 B1 comprising an electronically controlled capturing system for capturing data related to the amount of drug expelled from a reservoir by expelling means.

Especially if the device is designed to be self-contained, that is to say without a connector for a connection to an electrical power source which is necessary to provide electrical power for the operation of the device, the management of the resources of a power supply integrated into the device is particularly important.

PCT publications WO2021191322 and WO2021191327 disclose embodiments of electronic systems for drug delivery devices with improved power management. PCT publication WO2021191326 discloses an electronic system for a drug delivery device comprising a use detector unit and a drug delivery device comprising the electronic system.

The electronic system comprises a rotationally actuated switch (rotary switch) and an axially actuated switch (axial switch). The rotary switch indicates that dose delivery operation has begun.

However, it is possible that the rotary switch fails. In this case, the electronic system is not able to detect dose delivery operation in time or at all. This might result in malfunction of the electronic system and finally in risks for the health of a patient.

SUMMARY

It is an advantage of the present disclosure to reduce a risk of undetected malfunction of an electronic system for a drug delivery device and hence to decrease risks to the health of patients.

The drug delivery device comprises a dose setting and drive member, which is (at least in a final configuration) configured to perform a dose setting operation for setting a dose to be delivered by the drug delivery device and a dose delivery operation. The dose setting mechanism comprises a first member. The first member performs a specific movement relative to a second member during dose delivery operation.

The dose setting and drive mechanism may be based on the dose setting and drive mechanism disclosed in EP 2 890 435 A1, for example.

The second member may be mounted or mountable to the dose setting and drive mechanism such that the first member performs the specific movement relative to a second member during the dose delivery operation.

The drug delivery device may comprise the second member. For example, in one embodiment, the second member is (already) mounted to the dose setting and drive mechanism. The second member may be even formed integrally with a third member of the dose setting and drive mechanism that is different from the first member. Additionally or alternatively, the dose setting and drive mechanism may comprise the electronic system.

According to another aspect of the present disclosure, the second member may be provided separately from the dose setting and drive mechanism, for example as an individual component. In this case, the dose setting and drive mechanism and/or the second member are configured for mounting the second member to the dose setting and drive mechanism such the first member performs the specific movement relative to the second member during the dose delivery operation. The dose setting and drive mechanism may be only (fully) operable and/or (fully) functional if the second member is mounted thereto. In one embodiment, the second member is permanently mounted to the dose setting and drive mechanism once it is mounted thereto.

The dose setting and drive mechanism and the second member may constitute a system for assembling of the drug delivery device, wherein assembling the drug delivery device includes mounting the second member to the dose setting and drive mechanism.

Independently from whether the second member is initially mounted to the dose setting and drive mechanism (including the cases that the second member is integrally formed with the third member) or whether the second member is initially provided separately from the dose setting and drive mechanism and mounted to the latter later, the term "final configuration" denotes any configuration in which the second member is (finally) mounted to, mounted in, or integrated into the dose setting and drive mechanism, in which the dose setting and drive mechanism and a motion sensor system (described below) are fully operable, and in which the first member performs the specific movement to the second member during the dose delivery operation.

The dose setting and drive mechanism being operable includes that the dose setting and drive mechanism is operable for dose setting operation and dose delivery operation.

The electronic system comprises a first switch, a second switch, a sensor arrangement (for the motion sensor system), and an electronic control unit configured to control operation of the electronic system, wherein the electronic control unit is connected to the first switch, the second switch and the sensor arrangement. For example, the electronic control unit may be electrically connected with the first switch, the second switch, and the sensor arrangement.

(At least in the final configuration) the following applies:

the first switch is configured to be activated by a pre-defined operation;

the second switch is configured to indicate the specific movement of the first member relative to the second member; and the sensor arrangement is operable to provide position data that allows to distinguish between different positions of the first member relative to the second member.

The electronic system, for example the electronic control unit, is configured to perform (in the final configuration):

activate a failure detection functionality for detecting failure of the second switch if the first switch is activated whereas the second switch does not indicate the specific movement of the first member relative to the second member;

operate, in the failure detection functionality, the sensor arrangement; and determine failure of the second switch based on position data obtained from the sensor arrangement.

As noted above, the first member performs the specific movement relative to the second member during dose delivery operation. Vice versa, the progress of dose delivery operation requires the occurrence of the specific movement. Preferably, the specific movement occurs only during dose delivery operation.

As the second switch is configured to indicate (the occurrence) of the specific movement of the first member relative to the second member, the second switch is configured to detect when dose delivery operation is in progress. The electronic system may be configured to switch to a different state, for example to a measurement state as explained below, when the second switch indicates the specific movement (and hence that dose delivery operation is started and in progress).

If the second switch does not work properly, the electronic system might not switch to the different state (for example the measurement state as described below) or might switch to the different state too late. This may result in malfunction of the drug delivery device. The malfunction may confuse the user and/or endanger the health of a patient. The user might be patient or a health care professional (HCP) of the patient, for example.

If a common electronic system for drug delivery devices is employed in the drug delivery device, typically neither the common electronic system nor the user notices failure of the second switch as such or the malfunction instantly, for example at the next dose delivery operation after the failure of the second switch occurred for the first time. This may result in misconceptions of the user regarding the dose(s) delivered and/or the dose(s) required at this point of time or later. It is also possible that the misconception of the user and/or the malfunction of the device lead to maladjustments of medicament delivery schedules and/or of the titration of the medicament. This might finally result, for example, in an unintentional overdose resulting in a very dangerous hypoglycemic state of the patient.

The electronic system is able to detect (possible) failure of the second switch. This helps to avoid risks as pointed out above. For example, failure detection functionality may allow the electronic system to generate a failure alert, for example to the patient and/or HCP. The failure detection functionality also opens up the possibility to lock the electronic system or at least one functionality of the electronic system, for example a measurement of a dose delivered during dose delivery operation.

Summed up, the disclosed electronic system for a drug delivery reduces the risk of undetected malfunction of the electronic system and hence can support in decreasing risks to the health of patients.

The second switch is configured to be engaged by the specific relative movement of the first member relative to the second member. The second switch may be not directly engageable by the user in the final configuration (for example by directly touching and/or pressing it). Preferably, the second switch is (at least in the final configuration) located such that it is not accessible by the user. Especially, the second switch may be located in an interior of the drug delivery device.

The pre-defined operation may be a pre-defined user operation (for example, of operating the drug delivery device). According to a further aspect, the pre-defined user operation may consist of or include touching and/or pressing an actuation element. The actuation element may be, for example, a button, a button module, or a part of the button module, such as a proximal end face or proximal push button of the button module. The actuation element may be part of the drug delivery device, the dose setting and drive mechanism, the second member, and/or of the electronic system. Most preferably, the button module is the actuation element or comprises the actuation element.

In one embodiment, the actuation element is (at least concomitantly) pressed and/or touched by the user when starting, performing, and/or completing dose delivery operation. This may happen as a side effect and/or as an incidental effect but inevitably. Starting/triggering dose delivery operation may include a transition from dose setting operation to dose delivery operation. More preferably, the actuation element is pressed and/or touched by the user for starting/triggering, performing, and/or completing dose delivery operation.

In one embodiment, the first switch is configured to be (at least concomitantly) activated in conjunction with dose delivery operation (including starting/triggering, performing, and/or completing dose delivery operation).

In one embodiment, the pre-defined (user) operation (at least concomitantly) occurs in conjunction with dose delivery operation.

Each of the three embodiments according to the last three paragraphs (referred to as "activation implementations" in the following) respectively ensure that the failure detection functionality can be easily activated in conjunction with dose delivery operation. The user does not have to perform a completely different operation to make it possible that the failure detection functionality is activated. For any one of the activation implementations and any arbitrary combination of them, it is even expected that the first switch is activated (such that it is possible that the failure detection functionality is activated) even if the user simply performs dose delivery operation without a specific intention to activate the failure detection functionality, at least with a certain probability.

In general, the features
that the pre-defined user operation (at least concomitantly) occurs in conjunction with dose delivery operation and/or
that the actuation element is (at least concomitantly) pressed and/or touched by the user when starting, performing, and/or completing dose delivery operation
do respectively not mean or imply (but do not exclude) that the pre-defined user operation or pressing and/or touching the actuation element as such is sufficient for starting/triggering, performing, and/or completing dose delivery operation. For example, it may be additionally necessary to perform dose setting operation with setting a dose different from zero before dose delivery operation can be performed. Additionally or alternatively, it may be additionally required to unlock a locking mechanism (for preventing inadvertent dose delivery operation and/or dose delivery operation by unauthorized users) before a dose delivery operation can be performed.

Furthermore, the features of the activation embodiments in general do respectively not mean or imply (but does not exclude) that performing dose delivery operation is inevitable for activating the first switch. Preferably, activation of the first switch is possible without dose delivery operation. For example, the activation of the first switch may be possible in any, several, or all of the following conditions, in which no dose delivery operation can be performed:
no dose is set;
the locking mechanism is not unlocked; and
no medicament to be delivered is available, for example because a reservoir for containing the medicament (for example a cartridge) is empty or not mounted.

Apart from that, the features of the activation embodiments do respectively not mean or imply (but do not exclude) that activation of the first switch as such is causal for dose delivery operation. As noted above, the activation of the first switch may be simply concomitantly with starting/triggering, performing, and/or completing dose delivery operation.

In an embodiment, the first switch is configured such that the actuation element must be pressed and/or touched
for a longer, equal, or shorter time than it may be necessary for dose delivery operation,
with more, equal, or less force than it may be necessary for dose delivery operation, and/or
with a larger, equal, or smaller stroke than it may be necessary for dose delivery operation by the user for the first switch being activated.

According to a further aspect, the first switch and/or the electronic system may include a temporal and/or forced-base debouncing for activation of the first switch.

In one embodiment, the first switch is activated (at least concomitantly) by the user when starting, performing, and/or completing dose delivery operation. This ensures with high reliability that the failure detection functionality can be activated.

Preferably, the first switch comprises an axial switch, a foil switch, and/or a touch sensor. The touch sensor may include a capacitive sensor.

The term "axial switch" may indicate a component of a switch assembly and/or a switch that is configured to be actuated by an axial movement of two components relative to each other. An axial direction may be parallel to or correspond to a longitudinal direction of the drug delivery device.

For example, the axial switch may be actuated by axial movement between,
on the one hand, the first component and/or a first axial switching element, wherein the first axial switching element is at least axially fixed with regard the first component (at least in the final configuration), and,
on the other hand, the second component and/or a second axial switching element, wherein the second axial switching element is at least axially fixed with regard to the second component (at least in the final configuration).

Preferably, the first axial switching element (if any) is rotationally and axially fixed to the first member (at least in the final configuration). Preferably, the second axial switching element (if any) is rotationally and axially fixed to the second member (at least in the final configuration).

For example, the axial switch may be implemented according to any one of the respective embodiments disclosed in WO 2019/101962 A1, WO2021191322, WO2021191327, WO2021191326, and WO2021191325. These documents are incorporated by reference.

The first switch may be configured to generate a first signal when it is activated. The first signal may comprise and/or result from a change of an electrical resistance, capacity and/or inductivity of the first switch. The first signal may comprise an electrical signal, a change in an electric signal, a digital signal, and/or a change in a digital signal, for example.

In one embodiment, the first member rotates relative to the second member during dose delivery operation, wherein the second switch is a rotary switch configured to indicate rotation of the first member relative to the second member. In other words, the specific movement includes or consists of a (specific) rotation of the first member relative to the second member during dose delivery operation. The (specific) rotation during dose delivery operation may be only along a specific rotational direction, for example only clockwise or only anti-clockwise. More preferably, the specific rotation occurs only during dose delivery operation (but not, for example, during dose setting operation).

In one embodiment, the first member does not rotate relative to the second member during dose setting operation. Alternatively, the first member may rotate relative to the second member during dose setting operation in a rotational direction opposite to the specific rotational direction. The dose delivery device may be adapted in this manner. In particular, the dose setting and drive member and/or the second member may be configured accordingly.

The term "rotary switch" may indicate a component of a switch assembly and/or a switch that is actuated by rotational movement between two components, for example between, on the one hand, the first component and/or a first rotary switching element, wherein the first rotary switching element is at least rotationally coupled with regard to the first component (at least in the final configuration and during dose delivery operation), and, on the other hand, the second component and/or a second rotary switching element, wherein the second rotary switching element is at least rotationally fixed with regard to the second component (at least in the final configuration and during dose delivery operation).

Preferably, the first rotary switching element (if any) is rotationally and axially fixed to the first member (at least in the final configuration). Preferably, the second rotary switching element (if any) is rotationally and axially fixed to the second member (at least in the final configuration).

The first rotary switching element may be the same as the first axial switching component. The second rotary switching element may be the same as the second axial switching component.

The rotary switch may be implemented according to any one of the respective embodiments disclosed in WO2021191322, WO2021191326 and WO2021191325.

The second switch may be configured to generate a second signal when the first member performs the specific movement relative to the second member in the final configuration. The second signal may comprise and/or result from a change of an electrical resistance, capacity and/or inductivity of the second switch. The second signal may comprise an electrical signal, a change in an electric signal, a digital signal, and/or a change in a digital signal, for example.

The second switch can be a mechanically-actuated switch. In other words, the specific movement may mechanically trigger the second switch, e.g., trigger the generation of the second signal. Ongoing specific movement may continue to trigger the second switch. The second switch may be a mechanically-actuated electrical switch.

As noted above, the sensor arrangement is operable to provide position data that allows the electronic system to distinguish between different positions of the first member relative to the second member, for example between at least two successive relative rotational positions (along the specific movement), more preferably between at least four successive relative positions. The specific movement may cause change of the position of the first member relative to the second member.

Preferably, the different relative positions are different rotational positions of the first member relative to the second member.

According to a further aspect, the sensor arrangement may be configured to provide position data indicating an unambiguous, for example rotational, position of the first member relative to the second member. In one embodiment, the same position data will be provided only for one single angular position (range) of the first member relative to the second member.

In contrast to the sensor arrangement, the rotary switch might not provide position data.

Preferably, the sensor arrangement is configured to form, together with an encoder component, the motion sensor system (at least in the final configuration). In other words, the sensor arrangement is a sensor arrangement for the motion sensor system comprising (or consisting of) the sensor arrangement and the encoder component. The sensor arrangement may be adapted to use the encoder component for providing the position data.

According to an aspect of the present disclosure, the sensor arrangement (and hence the motion sensor system) comprises at least one of a light source with a corresponding optical sensor, an electrical sliding contact sensor, a mechanical switching arrangement, an inductive sensor, and/or a magnetic sensor, for example a magnetic field sensor. Especially, the sensor arrangement may comprise at least one light source and at least two optical sensors, wherein the sensor arrangement is configured to provide (in the final configuration) position data allowing to distinguish at least four different (successive) positions of the first member relative to the second member.

Preferably, the sensor arrangement (and optionally the whole motion sensor system) may be implemented according to any of the embodiments described in WO 2019/101962 A1, WO2021191327, WO2021191322, WO2021191326, and WO2021191325. More preferably, the sensor arrangement (and optionally the whole motion sensor system) is implemented according to any of the embodiments described in EP 20315305.1.

The encoder component may be a part of the dose setting and drive mechanism. The motion sensor system may become (fully) functional—such that the sensor arrangement can actually provide meaningful position data—by mounting the second component to the dose setting and drive mechanism. In this regard, the motion sensor system may be formed/completed by mounting the second component to the dose setting and delivery mechanism.

The second switch may be provided in addition to the sensor arrangement. The second switch and the sensor arrangement may be adapted to work, as such, independently of each other. The sensor arrangement and the second switch may be configured to produce different outputs. In particular, the sensor arrangement may be configured to generate an output that is different from the second signal generated by the second switch. The second switch may be separate from the sensor arrangement and vice versa.

According to one aspect, the sensor arrangement may be based on a measurement principle that is different from a principle of actuation of the second switch by the specific movement. For example, the second switch can be the mechanically-actuated switch (as mentioned above), wherein the sensor arrangement is an optical sensor arrangement comprising the at least one optical sensor. This ensures a particularly reliable detection of failures of the second switch.

In one embodiment, the specific movement includes or consists of an axial movement and the motion sensor system is a linear motion sensor system. The first member may be a piston rod or a drive sleeve for driving the piston rod during dose delivery operation, for example.

In one embodiment, specific movement includes or consists of the (specific) rotation and the motion sensor system is a rotary sensor system. The sensor arrangement may be at least rotationally fixed with regard to the second member. Especially, the sensor arrangement may be at least rotationally fixed (directly) to the second member. The encoder component may be at least rotationally fixed with regard to the first member. Especially, the encoder component may be rotationally fixed to the first member.

The sensor arrangement may be axially fixed with regard to the second member, preferably (directly) to the second member. The sensor arrangement may be formed integrally with the second component.

The encoder component may be axially fixed with regard to or (directly) to the first member. The encoder component may be formed integrally with the first component.

It may be considered that the encoder component is not part of the electronic system as such. In one embodiment, the encoder component (as such) does not include electrical parts (including electronic parts) of the electronic system. In particular, the sensor arrangement may comprise all active parts for the rotary sensor system, for example all electric and/or electronic parts. The encoder component may be a purely passive part. For example, the button module (which may comprise or constitute the second member) includes the electronic system and is provided separately (especially alone, without dose setting and drive mechanism); the electronic system may still be considered being complete even if the encoder component is not provided with the button module. In this regard, it may not matter if the sensor arrangement is not able to deliver meaningful position data without the encoder component.

Preferably, the sensor arrangement as such is not changed and/or modified by combining it with the encoder component to the motion sensor system. Additionally or alternatively, the encoder component as such is not changed and/or modified by combining it with the sensor arrangement to the motion sensor system.

Preferably, the electronic system is configured to deactivate the failure detection functionality if the second switch indicates the specific movement. Obviously, this indication proves that the second switch is functional.

According to another aspect, the electronic system is configured to determine, with the failure detection functionality, failure of the second switch if the position data obtained from the sensor arrangement with the failure detection functionality indicates that an extent of the specific movement of the first member relative to the second member
corresponds to a certain extent,
corresponds to at least the certain extent, or
exceeds the certain extent.

In particular, the certain extent may be zero and the electronic system is configured to determine, with the failure detection functionality, failure of the second switch if the position data obtained from the sensor arrangement with the failure detection functionality indicates that an extent of the specific movement exceeds zero. In other words, any specific movement that can be detected by the failure detection functionality leads to determining failure of the second switch.

In a preferred embodiment, the certain extent has a predetermined value that is greater than zero. The certain extent may correspond to a predetermined overall specific movement corresponding to a dispense of a certain amount of insulin during dose delivery operation, for example a predetermined fraction of one unit of insulin. Preferably, said fraction is in the range from 0.1 units to 2 units of insulin. By employing the predetermined value greater than zero, inappropriate determination of failure of the second switch due to harmless, limited specific movement that may occur due to mechanical variations and/or tolerances without actual dose dispense can be avoided.

The electronic control unit may be adapted to monitor, in the failure detection functionality, whether the first switch remains in its activating state and/or whether the second switch indicates specific movement.

For example, the electronic control unit may be configured to monitor the states of the first switch and the second switch as interrupts.

Preferably, the electronic system comprises an electrical power supply. The electrical power supply may comprise, for example, a rechargeable battery, a non-rechargeable battery, a solar cell, and/or an inductive power supply. The electrical power supply may be electrically connected at least with the electronic control unit.

The electronic control unit may be arranged on a conductor carrier and electrically conductively connected with conductors on the conductor carrier. The conductor carrier may be a circuit board such as a printed circuit board. The conductor carrier may be retained in the interior of a user interface member of the system or the device, for example in an interior of the dose setting and drive mechanism or an interior of the button module. The electric power supply may be arranged in the interior of the electronic system such as in the interior of the user interface member.

In one embodiment, the electronic system comprises a memory unit. In more detail, the electronic control unit may comprise the memory.

In one embodiment, the memory unit is non-volatile. Thus, even if the power supply to the electronic system is reduced and/or if the electronic system is switched off, information stored in the memory unit may still be available for subsequent operations.

The memory unit may be configured to store at least a measurement result regarding the dose delivered during a last dose delivery operation, and time information at least regarding the last dose delivery operation. Especially, the electronic system may be configured to automatically store at least a dose record for the latest dose delivery operation in the memory. Each dose record includes at least a time stamp (indicating date and time information) for the respective dose delivery operation and the size of the dose delivered by the respective dose delivery operation. More preferably, the memory unit is configured to store dose records regarding several last dose delivery operations, for example with respect to at least the last five dose delivery operations.

Additionally or alternatively, the memory unit may be configured for storing position data, time information related to position data, and/or time information regarding changes of the state of the electronic system, an indication for failure of the rotary switch, and/or a possible failure flag. The position data may comprise or consist of Gray code data.

In particular, the electronic system may be configured to store position data after dose delivery operation has been finished (preceding position data), respectively. In other words, the electronic system is configured to remember the position of the first member relative to the second member after the latest dose delivery operation has been completed.

The electronic system may be further configured to use, in the failure detection functionality, preceding position data (stored position data) and/or position data obtained from the sensor arrangement in the failure detection functionality for determining whether the extent of rotational movement of the first member relative to the second member corresponds to the certain extent, corresponds to at least the certain extent, or exceeds the certain extent.

Preferably the electronic control unit is configured to operate, in the failure detection functionality, the sensor arrangement at least when the first switch is released (when the first switch is no longer held activated). It is anticipated that drug delivery operation will not start directly after release of the first switch. In other words, it is anticipated that there will no specific movement directly after release of the first switch. Hence, the failure detection functionality can be deactivated. Naturally, the failure detection functionality can be activated again if the first switch is held activated again.

According to another aspect, the dose setting and drive mechanism is configured such that the overall specific movement of the first member relative to the second member during dose delivery operation corresponds to a dose delivered during dose delivery operation. For example, the dose delivered may correspond at least linearly to an extent of the overall specific movement during the respective dose delivery operation.

Preferably, the electronic control unit is configured to switch the electronic system to the measurement state when the second switch indicates the specific movement of the first member relative to the second member. This may at least apply if the electronic system is in any one of a sleep state and the failure detection functionality.

According to a further aspect, the electronic control unit may be configured
- to deactivate the failure detection functionality when switching to the measurement state if the failure detection functionality is active at this time and/or
- to not activate the failure detection functionality in the measurement state.

As switching to the measurement state may require the indication for the specific movement from the second switch, the second switch seems to be functional (functioning) if the electronic system switches to the measurement state. Apart from this, the problem that the sensor arrangement could be operated by the measurement state and by the failure detection functionality at the same time is reliably avoided.

The electronic system may be configured for operating the sensor arrangement in the measurement state to provide measurement data describing the specific movement of the first member relative to the second member.

Typically, measurement data may comprise a plurality of encoder readings.

The measurement state may be different from the failure detection state. Operation of the sensor arrangement in the measurement state may be different from operation of the sensor arrangement in the failure detection state.

More preferably, the electronic control unit is configured to determine the size of the dose delivered based at least on the measurement data obtained by operating the sensor arrangement in the measurement state. The dose delivered may be determined, for example calculated, based on (at least) the measurement data obtained by operating the sensor arrangement in the measurement state.

According to one aspect, the electronic control unit is prevented from determining the size of the dose in the failure detection state.

In one embodiment, the sensor arrangement is configured to provide the measurement data corresponding to a Gray code.

The electronic system may be configured to perform Gray code caching using the memory unit. This allows more energy-efficient and/or more reliable detection of failure of the second switch. Furthermore, this helps to increase the accuracy of measurements regarding doses delivered during dose delivery operation.

According to a further aspect of the present disclosure, the electronic control unit comprises a main microcontroller and a sensor controller.

For example, the electronic control unit may comprise or at least substantially consist of a Texas Instruments CC2640R2F or a similar device.

The main microcontroller may be configured to control the logic flow and the functional behaviour of the electronic system. This may include hardware input and user interface aspects (for example the first switch, the second switch, further buttons, and/or LEDs), power management, etc.

According to one aspect of the present disclosure, the electronic system is configured such that the main microcontroller wakes up (for example from the sleep state) when at least any one of the first switch and second switch is actuated.

The sensor controller may be an ultra-low power, low functionality processing core. It may be solely responsible for controlling the sensor arrangement (operating the sensor arrangement) in the measurement state. In addition, the sensor controller may be configured to take measurements to determine the dose delivered during drug delivery operation and/or to determine any errors or dose measurement with regard to these functions.

The electronic system may be configured that the sensor controller is awake (operated or switched on) only in the measurement state.

The electronic system might be configured such that the main microcontroller starts the sensor controller only when dose measurement begins as indicated by the second signal from the second switch. The main microcontroller may be also adapted to configure the sensor controller when dose measurement starts. The electronic control unit may continue the measurement state until it determines that dose delivery operation has completed. The sensor controller may finish operation when dose measurement stops. After dose delivery operation has ended, the electronic system might switch to another state, for example to a synchronization and/or pairing state (explained below).

According to a further aspect, the main microcontroller is not used for operating the sensor arrangement in the measurement mode. In one embodiment, the main microcontroller is not (configured to be) used for obtaining any position data used for measurement of the dose delivered itself. Such position data may be only provided through the sensor controller. The sensor controller may only be started (activated) when the second switch indicates the specific movement.

In one embodiment, the electronic system is controlled only by the main microcontroller at least in the failure detection functionality.

The electronic system may be configured such that the sensor controller is not operated (for example shut off) in at least the failure detection functionality. The electronic system may be configured such that the sensor controller is not operated in the sleep, the synchronization state, and/or the pairing state. This saves electrical power.

In a preferred embodiment, the main microcontroller operates the sensor arrangement in the failure detection functionality and wherein the sensor controller operates the sensor arrangement in the measurement state.

Preferably, the electronic system (in particular the electronic control unit) is configured to operate the sensor arrangement only in the failure detection functionality and the measurement state. In other words, the electronic system is configured such that the sensor arrangement is not operated (is shut off) in all states different from the measurement state when the failure detection functionality is not activated.

According to one aspect of the present disclosure, the electronic control unit is configured to operate the sensor arrangement in the measurement state with a measurement accuracy that is higher than in the failure detection functionality. Especially, the electronic control unit may be configured to operate the sensor arrangement in the measurement state with a higher sampling rate than in the failure detection functionality.

Additionally or alternatively, the electronic control unit is configured to operate the sensor arrangement in the measurement state with the sampling rate being at least 100 Hz. This ensures that the specific movement of the first member relative to the second member is sufficiently measured and described in detail even if the dose delivery operation is very fast.

The sensor controller then may store the measurement data, the measurement results, and/or associated diagnostic information in the memory unit (which is also accessible by the main microcontroller).

The electronic system may be configured such that the sensor controller stores the obtained measurement data (and optionally the diagnostic information) in the memory unit. In one embodiment, the sensor controller does not further evaluate the measurement data. In this case, the sensor controller is primarily or only used for quick and fast retrieval of measurement data.

In another embodiment, the sensor controller determines the size of the dose delivered (based at least on the measurement data). In other words, the sensor controller evaluates the measurement data. In this case, the sensor controller may be adapted to store the size of the dose delivered (and optionally the diagnostic information) in the memory unit.

According to another aspect, the electronic system may be configured that the main controller determines the size of the dose delivered (based at least on the measurement data).

It is also possible that the evaluation of the measurement data only occurs on request of the user and/or by a second device.

The sensor controller may store any data obtained and/or determined in the measurement state in a cache first and then forward it to the memory unit thereafter, for example when the electronic system switches out of the measurement state. For the latter, there may be an additional storage step after dose delivery operation has ended.

The electronic system, in particular the electronic control unit, may be configured to provide a dose record for the respective dose delivery operation. The dose record may include a time stamp for the respective dose delivery operation and the size of the dose delivered by the respective dose delivery operation. Additionally or alternatively, the dose record may include the diagnostic information. The electronic control unit may be configured to store the dose record in the memory unit and/or for transmission of the dose record via a communication unit (explained below).

In one embodiment, the electronic system comprises a communication unit for communicating with at least one second device. The communication unit may be configured to transmit data from the electronic control unit to the second device. Additionally or alternatively, the communication unit may be configured to receive data from the second device. For example, the second device includes or consists of a mobile phone, a tablet, a personal computer and/or another medical device, such as a blood glucose meter. The communication unit may be configured to transmit data such as position data,
date and/or time information related to position data,
dose records,
date and/or time information regarding changes of the state of the electronic system,
the indication for failure of the second switch,
and/or the possible failure flag.

According to a further aspect of the present invention, the communication unit is not operated (shut off) in the sleep state and/or in the measurement state. This reduces the electrical power consumption of the electronic system. Preferably, the communication unit is only operated (switched on) in a synchronization state and/or a pairing state.

The communication may be configured for wired transfer of data and/or for wireless transfer of data.

In one embodiment, the communication unit comprises a wireless communications interface for communicating with the second device via a wireless network such as Wi-Fi or Bluetooth®, and/or an interface for a wired communications link, such as a socket for receiving a Universal Serial Bus (USB), mini-USB or micro-USB connector.

For example, the communication unit may comprise a Bluetooth® core. The Bluetooth® core may be a non-programmable, fixed processing core. It may be configured to handle all low-level Bluetooth® communications functionality to prove the Bluetooth® interface for the main microcontroller to use.

According to a further aspect of the present disclosure, the electronic control unit may lock out at least one functionality and/or state of the electronic system when failure of the second switch has been determined. The at least one functionality and/or state may be no longer usable after failure of the second switch has been determined.

For example, the electronic system may be prevented from providing any measurement results regarding the doses delivered during dose delivery operations after the electronic control unit has determined failure of the second switch once. The electronic control unit may be configured to switch to a failure detected mode and/or to store a failure indication in the memory unit when failure of the second switch is prevented. In more detail, the electronic system may be prevented to switch to the measurement state after failure of the second switch has been determined. The electronic system may also block transmission of the position data, and/or measurement results (like the size of the dose delivered) regarding the dose delivered during the latest preceding dose delivery operation. It is possible that the second switch has not been working correctly at the time of the latest preceding dose delivery operation. In particular, the second switch might have indicated too late in the latest preceding dose delivery operation and the corresponding measurement result of the dose delivered might be incorrect.

The electronic system may even be configured to prevent any further operation of the electronic system except communication with the at least one second device after failure of the second switch has been determined (for example, the pairing state and/or the synchronization state may be still available). The electronic control unit may even perform permanent shutdown of the electronic system to prevent further use when failure of the second switch is determined.

Preferably, the electronic system is configured to activate (start) the failure detection functionality only when the first switch is (continuously) held activated for at least a predetermined time 'C'. The predetermined time 'C' may be a value in the range of 0.004 s to 0.4 s, preferably in the range of 0.03 to 0.3 s, for example 0.1 s. This reduces the risk that the electronic system is switched to the failure detection functionality by inadvertent operation of the button module. This helps to save electrical power.

A duration for which the first switch is held activated may be used to allow multiple different functionalities to be initiated by the same switch, e.g. switching to the synchronization state for a short duration of activation and release, and/or switching to a pairing state for a longer activation (and optionally release).

According to an aspect of the present disclosure, the electronic system is configured to switch to the pairing state
- if the first switch is (continuously) held activated, for example by (continuously) pressing the button module, for at least a predetermined time 'G' and is then released, and
- if, in addition, the second switch does not indicate the specific movement while the first switch is (continuously) held activated.

The predetermined time 'G' may be in the range from 3 s to 15 s, for example 3.5 s. This reduces the risk that the electronic system is switched to the pairing inadvertently. As dose delivery operation includes the specific movement, the electronic system will not enter the pairing state even if the first switch is (continuously) held activated during dose delivery operation for a longer time than time 'G' and is then deactivated. Accordingly, the electronic system will not even switch to the pairing state in case the first switch is still (continuously) held activated after the end of dose delivery operation and then released, irrespective of how long the first switch is still (continuously) held active after the end of dose delivery operation. This prevents inadvertent switching to the pairing state in conjunction with dose delivery operation is reliably prevented. Both criteria help to save electrical power and to avoid inadvertent pairing with wrong devices.

The pairing state may be for establishing data connection to the second device for allowing the transfer of data from the electronic system to the second device and/or from the second device to the electronic system.

The electronic system may be configured to automatically switch to the synchronization state after dose delivery operation has finished. For example, the electronic system may be configured to switch to the synchronization state when it switches out of the measurement state. Preferably, the electronic switches to the synchronization state automatically only if a new dose record is provided.

The synchronization state may be a state for transferring data from the electronic system to the second device and/or for transferring data from the second device to the electronic system. In particular, the synchronization state may be adapted for transmission of dose records to the other device. In more detail, the synchronization state may be adapted for completing, updating and/or synchronizing dose records stored in a memory of the second device with at least one dose record provided by the electronic system. The electronic and/or the second device may be configured accordingly. The at least one dose record provided by the electronic system may include a dose record provided as a result of a presently finished dose delivery operation and/or at least one dose record stored in the memory.

In one embodiment, the electronic system is configured to be manually switch to the synchronization state
- if the first switch is (continuously) held activated, for example by (continuously) pressing the button module, for at least a predetermined time 'F' and is then released and
- if, in addition, the second switch does not indicate the specific movement while the first switch is (continuously) held activated.

The predetermined time 'F' may be in the range from 0.5 s to 3 s, for example 0.5 s. This reduces the risk that the electronic system is switched to the synchronization state inadvertently. Additionally or alternatively, the predetermined time 'F' may be at least 1 s shorter than the predetermined time 'G'. As dose delivery operation includes the specific movement, the electronic system is not switched to the synchronization state manually even if the first switch is (continuously) held activated during dose delivery operation for a longer time than time 'F' and is then deactivated. Accordingly, the electronic system is not switched to the synchronization state manually in case the first switch is still (continuously) held activated after the end of dose delivery operation and then released, irrespective of how long the first switch is still (continuously) held active after the end of dose delivery operation. This prevents inadvertent switching to the synchronization state in conjunction with dose delivery operation is reliably prevented. Both criteria help to save electrical power and to avoid inadvertent manual switching to the synchronization state.

The functionality of manually switching the electronic system to the synchronization state and/or of switching to the pairing state may be the main functionality of the first switch. However, as the first switch is configured to be activated by the user in conjunction with dose delivery operation, the first switch is additionally used for activating the failure detection functionality. For example, the predetermined time 'C' may be less than the predetermined time 'G' (if provided) and less than the predetermined time 'F'.

The electronic system may be configured to automatically switch to the sleep state at the end of the synchronization state, and/or the pairing state.

According to a further aspect, the electronic control module may be configured to switch the electronic system to a certain state if the first switch is released while the failure detection is activated. The certain state may be the sleep state, the synchronization state, or the pairing state. It may be switched to different states depending on the duration how long the first switch has been held activated before it is released. The above explanations apply accordingly. This means, for example, that the failure detection functionality can be active while the first switch is held activated for the time interval 'G' for switching to the pairing state.

According to another aspect, the failure detection functionality can be active in parallel to the synchronization state and/or the pairing state. In another embodiment, the failure detection functionality is implemented as a separate failure detection state.

The drug delivery device may comprise a housing. In more detail, the dose setting and drive mechanism may include the housing. The housing retains and protects (the further components of) the dose setting and drive mechanism, for example from mechanical damages and dirt.

According to another aspect of the present disclosure, the dose setting and drive mechanism comprises a dial sleeve assembly. The dial sleeve assembly may rotate relative to the second member at least during dose delivery operation. The first member may be at least rotationally coupled to the dial sleeve assembly. In particular, the first member may be the dial sleeve assembly or a part of the dial sleeve assembly. In an embodiment, the dial sleeve assembly may not rotate relative to the second member during dose setting operation.

In one embodiment, the dial sleeve assembly is configured to rotate relative to the housing during dose setting operation and dose delivery operation. For example, the dial sleeve assembly may move on a helical path with regard to the housing during dose setting operation and dose delivery operation.

The dial sleeve assembly may include or consist of a number sleeve and/or a dial sleeve. The number sleeve and/or the dial sleeve may be threadedly engaged with regard to the housing. For example, the number sleeve may be threadedly engaged with the housing directly or to an insert that is axially and rotationally fixed to the housing. The number sleeve and/or the dial sleeve may comprise an inner thread or an outer thread for threaded engagement with the housing (insert).

The encoder component may comprise or consist of an encoder ring attached to the dial sleeve assembly. In more detail, the encoder ring may be attached to the dial sleeve.

According to a further aspect, a transition from dose setting operation to dose delivery operation may include that the first member and the second member become rotationally de-coupled with regard to each other.

In an embodiment, the dose setting and drive mechanism and/or the second member comprise at least one clutch. The second member and (the other parts of) the dose setting and drive mechanism can form the at least one clutch together. The at least one clutch may be configured such that the second member is rotationally coupled with regard to the first member during dose setting operation and/or that the second member is rotationally de-coupled with regard to the first member during dose delivery operation. The at least one clutch may be configured such that the transition from dose setting operation to dose delivery operation includes that the at least one clutch rotationally de-couples the second member and the first member, in particular from each other.

Additionally or alternatively, touching and/or pressing the actuation element may be necessary for transition from dose setting operation to dose delivery operation. In one embodiment, pressing the actuation element by an axial transition stroke (for example by the user and/or in the axial direction, preferably towards a distal direction of the drug delivery device) causes transition from dose setting operation to dose delivery operation. Pressing the actuation element by the axial transition stroke may disengage the at least one clutch.

According to another aspect, transition from the dose setting operation to the dose delivery operation may include at least first axial movement of (at least one part of) the second member relative to the first member. The first axial movement may be a predetermined relative movement parallel to a longitudinal axis of the drug delivery device and/or the dose setting and drive mechanism. Preferably, the first axial movement is a predetermined distal movement of the (at least one part) of the second member relative to the first member.

Additionally or alternatively, an activation stroke of (the at least one part of) the second member relative to the first member from an idle position may activate the first switch. The activation stroke may be parallel to the first axial movement. A length of the activation stroke may correspond to a length of the first axial movement times a factor TF. In generally, TF may be smaller than, equal to, or greater than 1. For example, TF may be in the range from 0.5 to 1.5.

At least one, several, or all electrical parts of the electronic system may be mounted to, fixed to and/or located within the dose setting and drive mechanism. This may especially apply if the second member is considered being a part of the dose setting and drive mechanism.

Preferably, the electronic system comprises or constitutes at least a part of the dose setting and drive mechanism. In other words, the electronic system may comprise a part of the dose setting and drive mechanism or the whole dose setting and drive mechanism. Regarding such embodiments, the term "electronic system" should not be limited to electrical parts (including electronic parts).

The second member may comprise the electronic system. The electronic system may be mounted to the second member. Especially, the electrical system may be mounted to, fixed to and/or located within the second member. Vice versa, the electronic system may comprise the second member.

In particular, the second member may comprise all electrical parts (including all electronic parts) of the electronic system. All electrical parts (including all electronic parts) of the electronic system may be mounted to, fixed to, and/or located within the second member. As explained above, the encoder component for the rotary sensor system may be considered not being an electrical part of the electronic system and hence not being part of the electronic system as such.

According to another aspect of the present disclosure, the drug delivery device and/or the electronic system comprises the button module.

The button module and/or the electronic control unit may have a distal surface facing towards the dose setting and drive mechanism, for example for providing an interface for mechanical interaction and/or electrical connection with further component parts of the system. As an example, the distal surface may comprise at least two, e.g. four, contact pads of the electronic control unit which may be selectively connected and disconnected with electronic components, such as switching components.

The button module may be permanently or detachably attached to a trigger, a button, or a dial grip, e.g. at or near the proximal end of the drug delivery device. In the final configuration, the button module may be located at a proximal end of the dose setting and drive mechanism. Especially, the button module may constitute a proximal end of the drug delivery device along the axial direction (at least in the final configuration).

For example, the button module includes the first switch, the second switch, the sensor arrangement for the rotary sensor system, and/or the electronic control module. The button module may comprise the electrical power supply and/or the communication unit.

According to another aspect, the button module may comprise or constitute the actuation element. For example, the actuation element may be a proximal end of the button module or the whole button module. For dose delivery operation, the user must touch and/or press on the button module. In more detail, the user must touch and/or press on the proximal end of the button module. The first switch can comprise, for example, a touch sensor, a foil switch, and/or a push button arranged at the proximal end of the button module.

Preferably, the second member is at least a part of a button module. Vice versa, the button module may be at least part of the second member. More preferably, the button module constitutes the second member. In other words, preferably the button module is the second member (and vice versa).

For example, in the device disclosed in EP 2 890 435, the button module may constitute the second member. During dose setting operation, the dial sleeve assembly (e.g. including the number sleeve and the encoder component) and the button module extend (translate) helically from a housing of the device. There is no relative rotation between the button module and the dial sleeve assembly during dose setting operation.

In said embodiment, the button module and the (at least one) clutch are translated distally relative to the housing for transition from the dose setting operation to dose delivery operation. After the clutch has translated a predefined distance, e.g. less than 2.0 mm, for example nominally 1.20 mm, the clutch disengages from the dial sleeve and the drug delivery device (in particular the dose setting and drive mechanism) enters a dispensing mode for drug delivery operation. During drug delivery operation, the dial sleeve assembly retracts back along the helical path into the device, whereas the button module does not rotate and only retracts with axial motion, until a 0 U (zero units) stop is engaged and the drug delivery operation is complete. Relative rotation of the button module with respect to the dial sleeve assembly occurs during dose delivery operation. In an exemplary embodiment, the second switch (rotary switch) is mounted in an underside (i.e. on a distal side) of the button module and utilises the relative rotation between the button module and dial sleeve assembly to trigger.

In this exemplary application to the device disclosed in EP 2 890 435, the first switch (axial switch) will also be triggered when the button module is pressed for dose delivery operation. It may be further possible that the axial switch will not be triggered before a point of clutch disengagement, e.g. 1.2 mm button module translation, so some rotation of the dial sleeve assembly may occur prior to the axial switch being activated.

Use of the second switch (in this embodiment the rotary switch) to initiate the measurement state ensures that the dose delivered is accurately recorded, irrespective of the axial position of the button module. Without the requirement to trigger prior to clutch disengagement, the maximum deflection of the axial switch contacts and therefore the forces, stresses and package space of this axial switch can be minimised.

According to one aspect of the present disclosure, when the button module is pressed, the button module is translated, e.g. together with the clutch, distally relative to the dial sleeve assembly. The nominal axial travel may be limited, e.g. to less than 3 mm, for example to between 1.5 mm and 2.0 mm, travel of the button module relative to the dial sleeve (and the encoder ring), further relative axial motion is limited.

According to a further aspect of the present disclosure, when the user releases the button module at the end of dose delivery operation, the button module and clutch translate proximally relative to the housing, e.g. under a clutch spring force. Consequently, the axial switch is released. Release of the axial switch in the measurement state indicates to the electronic control unit that the user has released the button module and that dose delivery operation has been finished. The electronic control unit may be configured to switch out of the measurement state if the axial switch is released in the measurement state. Without this information, an increased delay period would be required in prior to switching out of the measurement state, since the electronic system must wait to check for no further rotary switch signals and/or no further change of position data to determine if the dose is complete. This would have a negative implication on battery life and user experience.

According to a further aspect of the present disclosure, the electronic system is configured to provide a failure alert if failure of the second switch is determined. Providing the failure alert may include
generating a failure indicating signal, and preferably transmitting the failure indicating signal by means of the communication unit and/or
presenting a visual, audible, and/or tangible alert to a user.

The electronic system may comprise a display. For example, the display may be adapted to display any one of, several of, and/or all of the following:
The failure alert,
the measurement result regarding dose delivered in the last dose delivery operation,
date and/or time information,
an indication that the electronic system is in the failure detection functionality,
an indication that the electronic system is in the measurement state,
an indication that the electronic system is in the synchronization,
an indication that the electronic system is in the pairing state,
the current time,
an indication if the electrical power supply is low.

The electronic system may comprise an LED indicator connected to the electronic control unit. The LED indicator may include at least one indicator LED. Different indicator LEDs may emit different colours of light.

The electronic system may be configured to show the failure alert using LED indicator. Alternatively or additionally, the electronic system may be adapted to indicate when the electronic system is in at least one certain state. For example, the LED indicator may unambiguously indicate when the electronic system is in the measurement state and/or when the electronic system is in the pairing state. Different indications can differ from each other by use of different colours of light, by different spatial illumination patterns and/or by different illumination pattern sequences in time.

Especially, the above problem is further solved by a button module for a drug delivery device, the drug delivery device comprising a dose setting and drive mechanism, which is configured to perform a dose setting operation for setting a dose to be delivered by the drug delivery device and a dose delivery operation for delivering the set dose and comprises a first member, wherein the first member performs a specific movement relative to the button module during the dose delivery operation. The button module comprises an electronic system according to any one of the embodiments described, wherein the button module is the second member.

The explanations of embodiments, modifications, and advantages regarding the electronic system apply accordingly concerning the button module as well, and vice versa. Especially, explanations of embodiments, modifications, and advantages concerning the second member apply accordingly to the button module.

In more detail, the button module may be integrated into, mounted to and/or mountable to the dose setting and drive mechanism such that the first member performs the specific movement relative to the button module during the dose delivery operation.

In one embodiment, the button module is (already) mounted to the dose setting and drive mechanism. The button module may be even formed integrally with a third member of the dose setting and drive mechanism that is different from the first member.

Alternatively, the button module may be provided separately from the dose setting and drive mechanism, for example as an individual component.

The button module may move axially relative to the first member during the transition from dose setting operation to dose delivery operation, or when the button module is pressed in a 0 U dialled condition.

As explained above, the first member, for example the dial sleeve assembly, may comprise the encoder component. More preferably, the encoder component may be part of or fixed to the number sleeve.

The dose setting and driving mechanism may be only (fully) functional if the button module is mounted. Especially, the electronic system may be only (fully) functional in this case, for example because the sensor arrangement is fixed to the button module whereas the encoder component is fixed to the first member (e.g. dose dial sleeve or component thereof) of the dose setting and drive member. Nevertheless, as explained above, the electronic system as such may be considered complete and ready if only the button module is provided: Preferably, the encoder component is no electrical component and/or not intended to be directly electrically connected to the electrical control unit.

The above problem is further solved by a drug delivery device comprising the electronic system according to any one of the embodiments described and/or the button module (with the electronic system) according to any one of the embodiments described.

The explanations of embodiments, modifications, and advantages regarding the electronic system, the button module, and the dose setting and drive mechanism apply accordingly concerning the drug delivery device as well, and vice versa. The explanations regarding embodiments, modifications, and advantages regarding the drug delivery device in this disclosure may apply regarding this embodiment as well.

For example, in one embodiment, the dose setting and drive mechanism further comprises the housing, wherein first member is the dial sleeve assembly or at least rotationally coupled to the drive sleeve assembly, wherein the dial sleeve assembly is rotatable relative to the housing, e.g. along a helical path, at least during dose delivery operation.

In one embodiment, the second member is the button module, wherein the button module is axially displaceable relative to the first member, and wherein the button module is rotationally constrained to the housing at least in the dose delivery operation. The button module may be rotatable with respect to the housing in the dose delivery operation, for example together with the dial sleeve assembly along the helical path.

According to a further aspect of the present disclosure, the drug delivery device further comprises a container receptacle, which is permanently or releasably connected to the dose setting and drive mechanism and which is adapted to receive a container containing a medicament.

The above problem is further solved by a method for operating an electronic system for a drug delivery device,
wherein the drug delivery device comprises a dose setting and drive mechanism, which is configured to perform a dose setting operation for setting a dose to be delivered by the drug delivery device and a dose delivery operation for delivering the set dose and comprises a first member, wherein the first member performs a specific movement relative to a second member during a dose delivery operation,
wherein the electronic system comprises a first switch, a second switch, a sensor arrangement of a motion sensor system, and an electronic control unit configured to control operation of the electronic system, wherein the electronic control unit is connected to the first switch, the second switch, and the sensor arrangement;
wherein:
the first switch is configured to be activated by a pre-defined operation;
the second switch is configured to indicate the specific movement of the first member relative to the second member; and
the motion sensor system is adapted to provide, by operating the sensor arrangement, position data that allows to distinguish between different positions of the first member relative to the second member;
characterized in that the method comprises at least the following steps:
activating a failure detection functionality for detecting failure of the second switch of the electronic system if the first switch is held activated whereas the second switch does not indicate the specific movement of the first member relative to the second member;
operating, in the failure detection functionality, the sensor arrangement; and
determining failure of the second switch based on position data from the sensor arrangement.

The explanations of embodiments, modifications, and advantages regarding the electronic system, the button module, the dose setting and drive mechanism, and the drug delivery device apply accordingly concerning the drug delivery device as well, and vice versa.

The present invention is particularly applicable for drug delivery devices which are manually driven, e.g. by a user applying a force to the button module, for devices which are driven by a spring or the like, and for devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrom.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1:2014(E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

The terms "axial", "radial", or "circumferential" as used herein may be used with respect to a main longitudinal axis of the device, the cartridge, the housing or the cartridge holder, e.g. the axis which extends through the proximal and distal ends of the cartridge, the cartridge holder or the drug delivery device.

The disclosure is not restricted to the subject matter defined in the appended claims. Rather, the disclosure may comprise improvements in addition or as an alternative to the ones defined in the independent claims as will become apparent from the following description.

BRIEF DESCRIPTION OF THE DRAWINGS

Non-limiting, exemplary embodiments of the invention will now be described with reference to the accompanying drawings, in which.

In the figures, identical elements, identically acting elements, or elements of the same kind may be provided with the same reference numerals.

DETAILED DESCRIPTION

Figure 1:
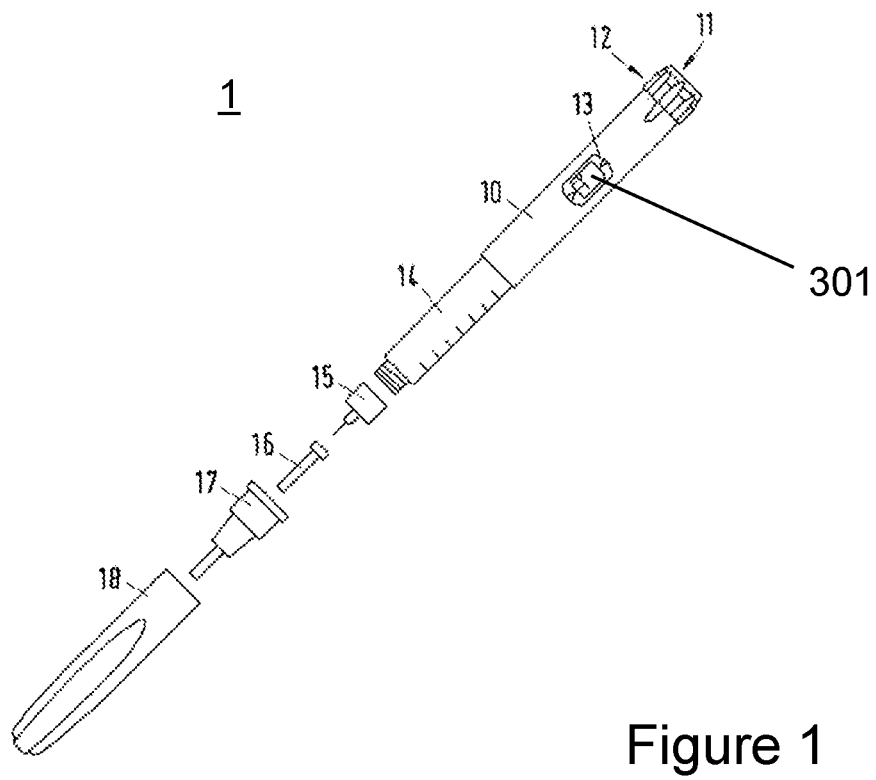
FIG. 1 shows an embodiment of a drug delivery device.

In the following, some embodiments will be described with reference to an insulin injection device. The present disclosure is, however, not limited to such application and may equally well be deployed with injection devices that are configured to eject other medicaments or drug delivery devices in general, preferably pen-type devices and/or injection devices.

Embodiments are provided in relation to injection devices, in particular to variable dose injection devices, which record and/or track data on doses delivered thereby. These data may include the size of the selected dose and/or the size of the dose actually delivered, the time and date of administration, the duration of the administration and the like. Features described herein include the arrangement of sensing elements and power management techniques (e.g. to facilitate small batteries and/or to enable efficient power usage).

Certain embodiments in this document are illustrated with respect to the injection device disclosed in EP 2 890 435 where an injection button and grip (dose setting member or dose setter) are combined. The injection button may provide the user interface member for initiating and/or performing a dose delivery operation of the drug delivery device. The grip or knob may provide the user interface member for initiating and/or performing a dose setting operation. Both devices are of the dial extension type, i.e. their length increases during dose setting. Other injection devices with the same kinematical behaviour of the dial extension and button during dose setting and dose expelling operational mode are known as, for example, the Kwikpen® device marketed by Eli Lilly (e.g. as described in WO2005018721) and the Novopen® 4 device marketed by Novo Nordisk (e.g. as described in U.S. Pat. No. 6,663,602). An application of the general principles to these devices therefore appears straightforward and further explanations will be omitted. However, the general principles of the present disclosure are not limited to that kinematical behaviour. Certain other embodiments may be conceived for application to an injection device where there are separate injection button and grip components/dose setting members, e.g. an injection device as described in WO2004078239. Thus, there may be two separate user interface members, one for the dose setting operation and one for the dose delivery operation.

"Distal" is used herein to specify directions, ends or surfaces which are arranged or are to be arranged to face or point towards a dispensing end of the drug delivery device or components thereof and/or point away from, are to be arranged to face away from or face away from the proximal end. On the other hand, "proximal" is used to specify directions, ends or surfaces which are arranged or are to be arranged to face away from or point away from the dispensing end and/or from the distal end of the drug delivery device or components thereof. The distal end may be the end closest to the dispensing and/or furthest away from the proximal end and the proximal end may be the end furthest away from the dispensing end. A proximal surface may face away from the distal end and/or towards the proximal end. A distal surface may face towards the distal end and/or away from the proximal end. The dispensing end may be the needle end where a needle unit is or is to be mounted to the device, for example.

FIG. 1 is an exploded view of a medicament delivery device or drug delivery device. In this example, the medicament delivery device is an injection device 1, e.g. a pen-type injector, such an injection pen disclosed in EP 2 890 435.

The injection device 1 of FIG. 1 is an injection pen that comprises a housing 10 and contains a container 14, e.g. an insulin container, or a receptacle for such a container. The container may contain a drug. A needle 15 can be affixed to the container or the receptacle. The container may be a cartridge and the receptacle may be a cartridge holder. The needle is protected by an inner needle cap 16 and either an outer needle cap 17 or another cap 18. An insulin dose to be ejected from injection device 1 can be set, programmed, or 'dialled in' by turning a dosage knob or dial grip 12, and a currently programmed or set dose is then displayed via dosage window 13, for instance in multiples of units. The indicia displayed in the window may be provided on a number sleeve or dial sleeve. For example, where the injection device 1 is configured to administer human insulin, the dosage may be displayed in so-called International Units (IU), wherein one IU is the biological equivalent of about 45.5 micrograms of pure crystalline insulin (1/22 mg). Other units may be employed in injection devices for delivering analogue insulin or other medicaments. It should be noted that the selected dose may equally well be displayed differently than as shown in the dosage window 13 in FIG. 1.

The dosage window 13 may be in the form of an aperture in the housing 10, which permits a user to view a limited portion of number sleeve 301 of a dial sleeve assembly that is configured to move when the dial grip 12 is turned, to provide a visual indication of a currently set dose. The dial grip 12 is rotated on a helical path with respect to the housing 10 when setting a dose.

In this example, the dial grip 12 includes one or more formations to facilitate attachment of a data collection device. Especially, the dial grip 12 may be arranged to attach a button module 11 onto the dial grip 12. As an alternative, the dial grip may comprise such a button module of an electronic system.

The injection device 1 may be configured so that turning the dial grip 12 causes a mechanical click sound to provide acoustic feedback to a user. In this embodiment, the dial grip 12 also acts as an injection button. When needle 15 is stuck into a skin portion of a patient, and then dial grip 12 and/or the attached button module 11 is pushed in an axial direction, the insulin dose displayed in dosage display window 13 will be ejected from injection device 1. When the needle 15 of injection device 1 remains for a certain time in the skin portion after the dial grip 12 is pushed, the dose is injected into the patient's body. Ejection of the insulin dose may also cause a mechanical click sound, which may be different from the sounds produced when rotating the dial grip 12 during dialling of the dose.

In this embodiment, during delivery of the insulin dose, the dial grip 12 is returned to its initial position in an axial movement, without rotation, while the number sleeve 301 is rotated to return to its initial position, e.g. to display a dose of zero units. FIG. 1 shows the injection device 1 in this 0U dialled condition. As noted already, the disclosure is not restricted to insulin but should encompass all drugs in the drug container 14, especially liquid drugs or drug formulations.

Injection device 1 may be used for several injection processes until either the insulin container 14 is empty or the expiration date of the medicament in the injection device 1 (e.g. 28 days after the first use) is reached. In the case of a reusable device, it is possible to replace the insulin container.

Furthermore, before using injection device 1 for the first time, it may be necessary to perform a so-called "prime shot" to remove air from insulin container 14 and needle 15, for instance by selecting two units of insulin and pressing dial grip 12 while holding injection device 1 with the needle 15 upwards. For simplicity of presentation, in the following, it will be assumed that the ejected amounts substantially correspond to the injected doses, so that, for instance the amount of medicament ejected from the injection device 1 is equal to the dose received by the user. Nevertheless, differences (e.g. losses) between the ejected amounts and the injected doses may need to be considered.

As explained above, the dial grip 12 also functions as an injection button so that the same component is used for dialling/setting the dose and dispensing/delivering the dose. As an alternative (not shown), a separate injection button may be used which is axially displaceable, at least a limited distance, relative to the dial grip 12 to effect or trigger dose dispensing.

In the following, an electronic system 100 for a drug delivery device according to the invention will be described with respect to exemplary embodiments.

The electronic system 100 may be implemented in a drug delivery device. In particular, the drug delivery device may include the electronic system 100 shown in FIG. 2. For example, the electronic system 100 may be provided in the injection device 1 of FIG. 1.

In general, the drug delivery device comprises a dose setting and drive mechanism 300 with a first member 20. The drug delivery device further comprises a second member. The first member 20 rotates relative to the second member during the dose delivery operation. The first member 20 may be a dial sleeve assembly or a part thereof. For example, the first member 20 may be a dial sleeve 302 of the injection device 1. The dial sleeve 302 may be axially and rotationally fixed to the number sleeve 301. The number sleeve 301 and the dial sleeve 302 may be even formed unitary or be the same component.

The second member may be part of the dose setting and drive mechanism 300 as well. However, preferably, the second member is a button module 11, for example as for the injection device 1 shown in FIG. 1. Typically, the button module 11 is mounted to the dose setting and drive mechanism 300. In more detail, the button module 11 may be axially and rotationally fixed to a member of the dose setting and drive mechanism 300, for example to a drive sleeve, a clutch sleeve, or the like.

As in the injection device 1 in FIG. 1, the button module 11 may constitute a proximal end of the drug delivery device.

The electronic system 100 includes an electronic control unit 110. The electronic control unit 110 may comprise or consist of a PCBA or be part of a PCBA. The electronic control unit 110 is configured to control operation of the electronic system 100.

The electronic system 100 further comprises at least one first switch that is operatively connected to the electronic control unit 110. In the embodiments shown, the first switch is an axially activated switch 220 (referred to as axial switch 220 in the following). The axial switch 220 may be configured to be activated by a pre-defined user operation that includes a certain operation that is necessary for starting/triggering, performing, and/or completing dose delivery operation.

For example, the axial switch 220 may be closed at least while the button module 11 is pressed, for example due to a mechanical design of the button module 11 and/or the dose setting and drive mechanism 300. In a modification, the first switch is a touch sensor, a push button, and/or a foil switch located at a cover 51 of the button module 11. The cover 51 constitutes a proximal end of the button module 11. The user must touch onto and press onto the cover 51 to push the button module 11 distally relative to the second member 20. In this case, the first switch is activated when the user touches and/or presses onto the cover 51. The cover 51 may be denoted as an actuation element of the button module 11.

Limited axial movement of the button module 11 relative to the first member 20 may be allowed.

The transition from the dose setting operation to the dose delivery operation may include that the button module 11 is moved, relative to the first member 20, from an initial relative position by at least an axial transition stroke along the axial direction, for example distally.

In one embodiment, the axial switch 220 is configured to switch from an idle state to an activating state by an activation stroke of the button module 11. Pressing the button module 11 from the initial relative position towards the first member 20 (relative to the latter) by at least the activation stroke brings the axial switch 220 from the idle state to the activating state. It may be necessary that the user must keep pressing the button module 11 to hold the axial switch 220 activated (in its activating state).

The button module 11 may be in its initial relative position with regard to the first member 20 at least during dose setting operation.

A restoring force may urge the button module 11 towards its initial relative position, for example proximally. The initial relative position of the button module 11 can be, for example, a most proximal position of the button module 11 relative to the first member 20.

The restoring force may be provided from at least one elastic member. The dose setting and drive mechanism 300 and/or the button module 11 can comprise the at least one restoring member. For example, the dose setting and drive mechanism 300 may comprise a clutch spring providing restoring force for the button module 11, the button module 11 may comprise a resilient element such as a spring providing restoring force for the button module 11, and/or the axial switch 220 itself provides restoring force for the button module 11.

The axial switch 220 may be configured to switch between a broken circuit state and a closed circuit state. In the closed circuit state, the axial switch 220 closes an electric circuit. In the broken circuit state, the axial switch 220 breaks the electric circuit.

In one embodiment, the activation stroke of the button module 11 relative to the first member 20 switches the axial switch 220 from the broken circuit state to the closed circuit state. The axial switch 220 may remain in the closed circuit state as long as the button module 11 is kept in an activating relative position. The activating relative position may be an activating relative position range. The activating relative position range may include all axial positions of the button module 11 relative to the first member 20 between the initial relative position plus the activation stroke on the one hand and a maximum stroke position of the button module 11 (relative to the first member 20) on the other hand.

Bringing the button module 11 to the maximum stroke position requires an axial movement of the button module 11 relative to the first member 20, which is in the same direction than the activation stroke but is larger than the transition stroke.

In an embodiment, the axial switch 220 is in the broken circuit state whenever the relative axial position of the button module 11 is closer to the initial relative position than a length of the activation stroke. The axial switch 220 is in the closed circuit state when the button module 11 is within the active relative position (range). In an alternative embodiment, the activation stroke of the button module 11 relative to the first member 20 switches the axial switch 220 from the closed circuit state to the broken circuit state. The axial switch 220 may remain in the broken circuit state as long it is kept in the activating relative position range and be in the closed circuit state else.

The activation stroke may be larger than, equal to, or smaller than the transition stroke. In other words, the activation stroke may include the transition stroke, the transition stroke may include the activation stroke or the activation stroke may be the same as the transition stroke. In any case, as the transition stroke (which necessary for starting dose delivery operation) and the activation stroke are parallel to each other and in the same direction, the user can easily activate the first switch in conjunction with dose delivery operation.

It is anticipated that the user typically presses the button module 11 to the maximum stroke position at least once in conjunction with dose delivery operation, for example in order to complete dose delivery operation. Hence, it is anticipated that the first switch is typically activated in conjunction with dose delivery operation even if the activation stroke is larger than the transition stroke. It is not a problem for the measurement of the size of the dose delivered that the first switch might be not activated before or at the beginning of dose delivery operation in some embodiments: Switching to the measurement state does not require that the first switch (axial switch 220) is activated.

In one embodiment, the transition stroke of the button module 11 (which is necessary and sufficient for completing the transition from the dose setting operation to the dose delivery operation) is larger than the activation stroke. This ensures that the axial switch 220 indicates that the user intends dose delivery operation a bit before the dose delivery operation actually starts. The electronic system 100 can activate a failure detection functionality even before the dose delivery operation could actually start. However, this is not necessary in general.

In another embodiment, the activation stroke is larger than the transition stroke. Additionally or alternatively, activation of the axial switch 220 may require that the user presses the button module 11 with at least a pre-defined force and/or for at least a pre-determined time. This ensures that the failure detection function can be only activated if rotation of the first member 20 relative to the second member (button module 11) is already possible. Unnecessary activation of the failure detection functionality can be prevented. This may save electrical energy.

The dose setting and drive mechanism 300 and/or the button module 11 may comprise at least one clutch. The clutch may be configured such that the transition stroke causes that the first member 20 (e.g. the dial sleeve assembly or a part thereof, for example the number sleeve 301) becomes rotationally decoupled from the button module 11.

It is noted that axial movement of the button module 11 relative to the first member 20 may happen not only for the transition from the dose setting operation to the dose delivery operation of the drug delivery device 1. In particular, the activation stroke of the button module 11 relative to the first member 20 may be also possible in a 0 U dialled condition of the drug delivery device 1 (if no dose is set). Hence, it may be possible to press the button module 11 to move distally prior to dose setting as well. Naturally, no dose delivery operation can be started in this case.

The electronic system 100 also comprises a second switch. In the exemplary embodiments, the second switch includes or consists of a rotationally activated switch 230 (referred to as rotary switch 230 in the following) that is operatively connected to the control unit 110. The rotary switch 230 is configured to indicate rotation of the first member 20 relative to the button module 11. For example, rotation of the first member 20 relative to the button module 11 may cause the rotary switch 230 to switch between a broken circuit state and a closed circuit state thereof. The rotary switch 230 may be mechanically actuated from said relative rotation (as schematically indicated by arrow 322 in FIG. 3B).

Contacts of the rotary switch 230 may be connected to the electronic control unit 110. The electronic control unit 110 may monitor this electrical connection to determine the circuit state of the rotary switch 230. A failure of the rotary switch 230 may, for example, result from a failure in said physical connectivity.

In embodiments, in which the first member 20 moves longitudinally relative to the second member during dose delivery operation, for example towards the distal direction, the second switch may include or consist of a switch activated by such longitudinal movement (longitudinal movement switch, not shown).

Figure 2:
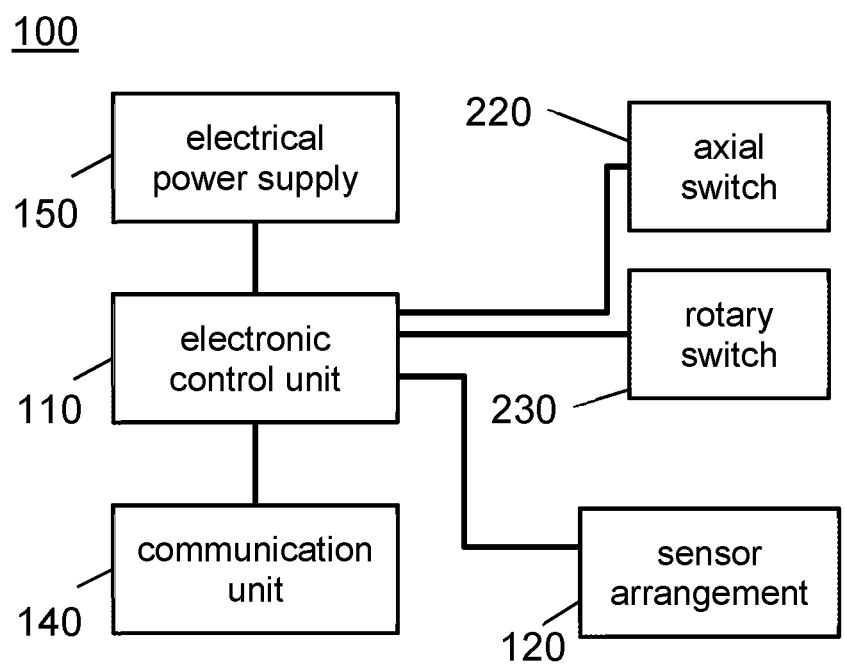
FIG. 2 schematically shows an embodiment of an electronic system according to the present disclosure.

As shown in FIG. 2, the electronic system 100 may further comprise an electrical power supply 150, e.g. a rechargeable or non-rechargeable battery.

The electronic system 100 may include a, preferably permanent and/or non-volatile, storage or memory unit 112. The memory unit 112 may be configured to store data related to the operation of the drug delivery device 1 such as dose history data, for example.

The electronic system 100 may further comprise a communication unit 140 for communicating with a second device. The communication unit 140 may be active only in a pairing state and a synchronization state in order to save electrical energy.

Unless specifically disclosed otherwise in the following, the electronic system 100 may have the functions and may be arranged and/or designed as described in WO 2019/101962 A1, WO2021191327, WO2021191322, WO2021191326, and WO2021191325, the disclosure of which is incorporated herein by reference.

For example, the axial switch 220 may be implemented according to any one of the respective embodiments disclosed in WO 2019/101962 A1, WO2021191322, WO2021191327, WO2021191326, and WO2021191325.

The rotary switch 230 may be implemented according to any one of the respective embodiments disclosed in WO2021191322, WO2021191326, and WO2021191325.

The electronic system 100 further includes a sensor arrangement 120 for a rotary sensor system 129. The sensor arrangement 120 is connected to the electronic control unit 110.

Figure 3A:
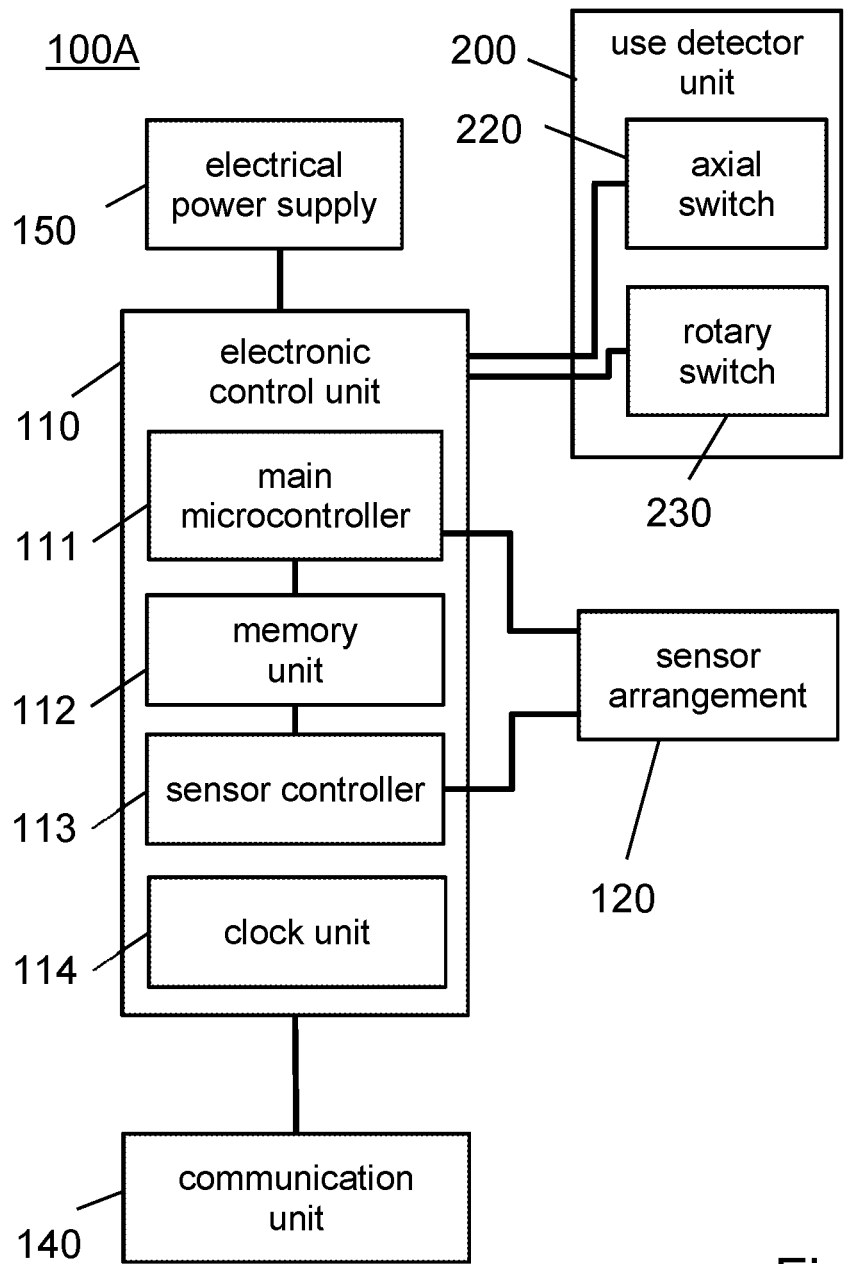
FIG. 3A schematically shows second embodiment of an electronic system according to the present disclosure.
Figure 3B:
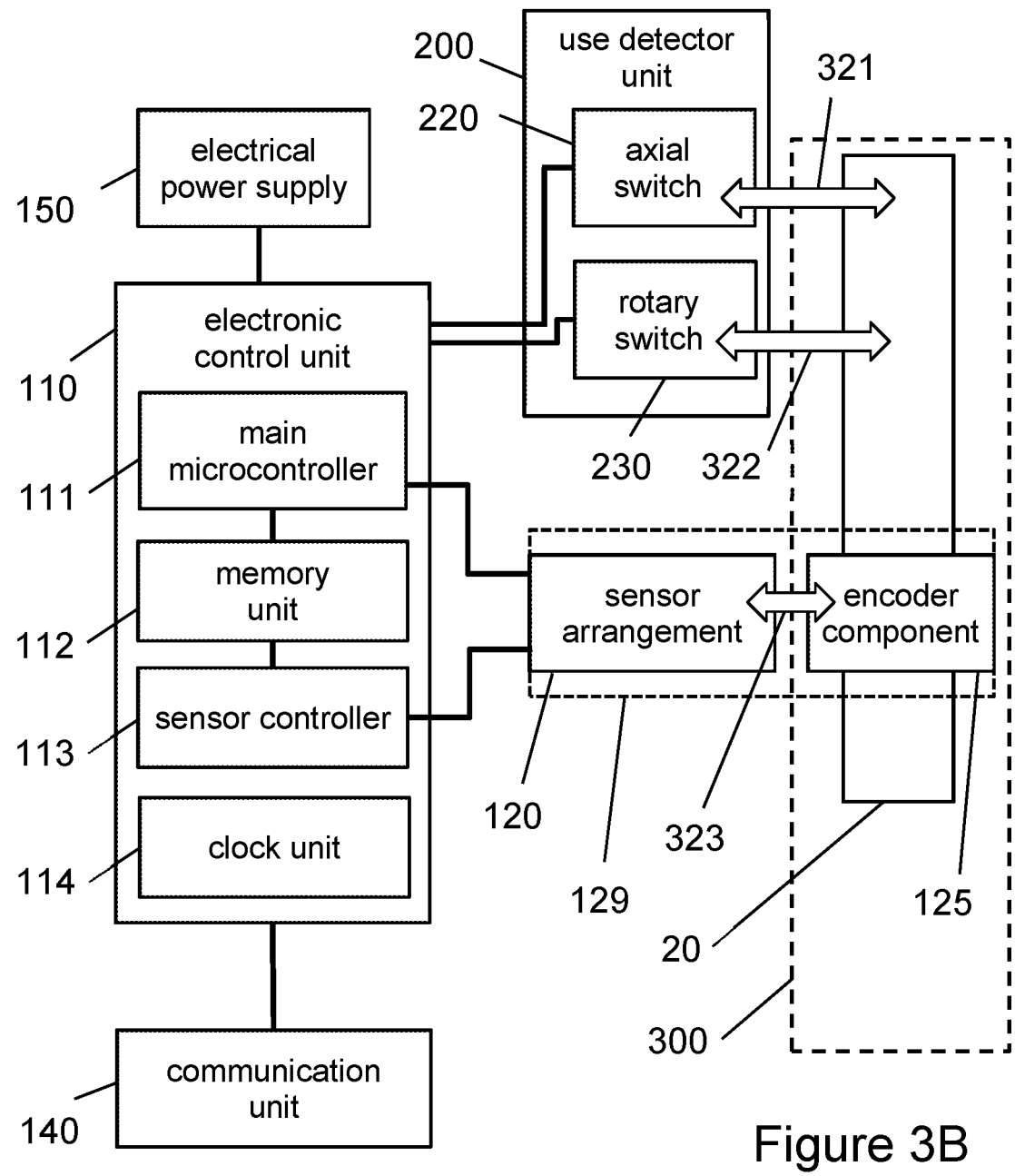
FIG. 3B schematically shows the electronic system of FIG. 3A together with a dose setting and drive mechanism of a drug delivery device.

The rotary sensor system 129 may comprise the sensor arrangement 120 and an encoder component 125 (see FIG. 3B). The encoder component 125 may be at least rotationally coupled to the first member 20. Preferably, the encoder component 125 is axially and rotationally fixed to the first member 20 as in FIG. 9. The encoder component 125 may be formed integrally with the first member 20.

Figure 9:
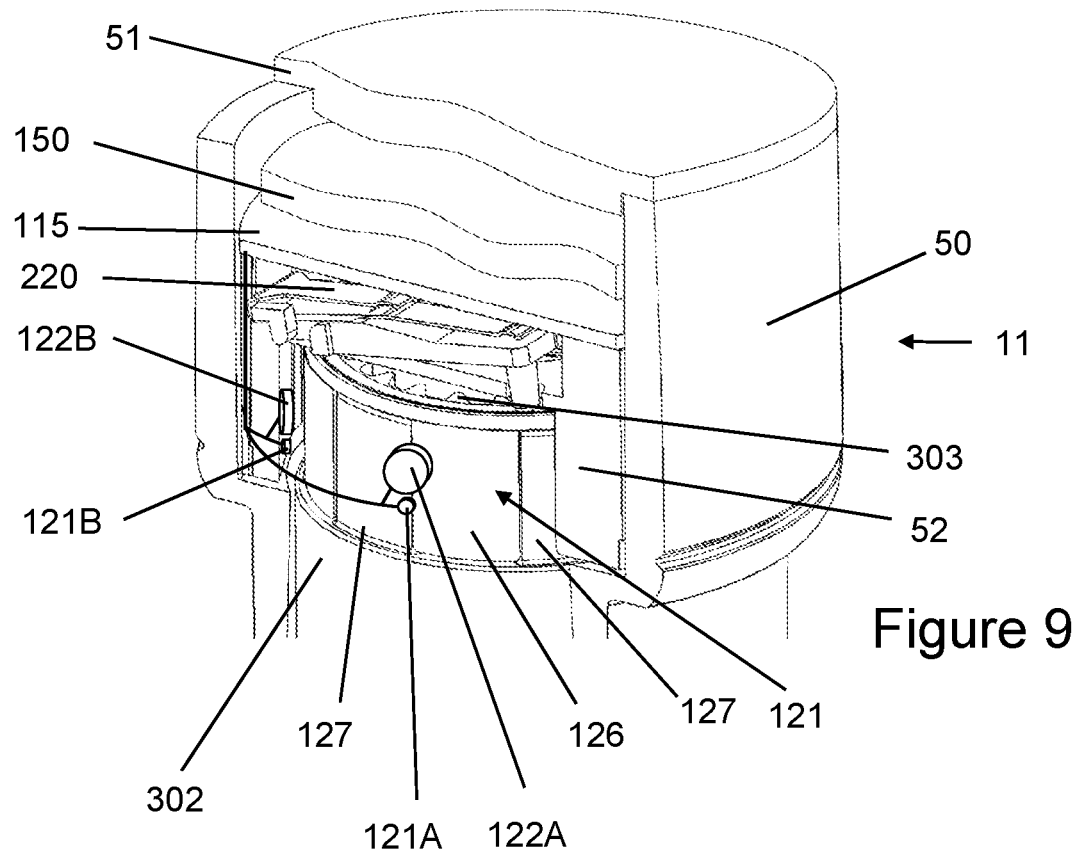
FIG. 9 shows a button module with an electronic system according to the present disclosure.

The sensor arrangement 120 may comprise one or a plurality of sensors 122A, 122B. Preferably, the sensor arrangement 120 comprises at least two sensors 122A, 122B as shown in FIG. 9. The at least two sensors 122A, 122B may be optoelectronic sensors for detecting electromagnetic radiation, such as IR sensors. The sensors 122A, 122B may be angularly separated (in particular along a circumferential direction around an axis of relative rotation between the first member 20 and the button module 11 as in FIG. 9). The sensor arrangement 120 may additionally comprise at least one radiation emitter 121A, 121B which emits radiation to be detected by the sensor. Each sensor 122A, 122B may have an associated radiation emitter 121A, 121B as shown in FIG. 9. In particular, the encoder component 125 may comprise a plurality of angularly separated detection regions 126. The detection regions may have a higher reflectance for the emitted radiation than regions in-between adjacent detection regions (also referred to as non-detection regions 127). Depending on the relative rotational position between the first member 20 and the second member (button module 11), the detection regions 126 face different sensors 122A, 122B. Hence, it depends on said relative rotational position which of the sensors 122A and 122B detect a high reflection of radiation. A detection pattern, which of the sensors 122A, 122B detect high reflection, depends on and changes with said rotational position. Hence, the detection pattern is indicative of said relative rotational position.

However, other rotary sensor systems can be employed as well. For example, the rotary sensor system 129 may include or consists of a magnetic rotary sensor system, a mechanical rotary sensor system and/or an inductive rotary sensor system.

The sensor arrangement 120 is operable by the electronic control unit 110 to generate (provide) measurement data describing rotational movement of the first member 20 of the dose setting and drive mechanism 300 relative to the button module 11. The electronic system 100—in particular the electronic control unit 110—uses the rotary sensor system 129 by operating the sensor arrangement 120.

In general, position data from the sensor arrangement 120 should enable to distinguish at least between two subsequent rotational positions of the first member 20 relative to the second member (e.g. the button module 11). Preferably, position data from the sensor arrangement 120 allows the electronic control unit 110 to distinguish between at least four different, subsequent rotational positions of the first member 20 relative to the second member (e.g. the button module 11) (for example with regard to method 600 shown in FIG. 6 and method 700 shown in FIG. 7). In some embodiments, position data from the sensor arrangement 120 may even allow to measure an absolute rotational position of the first member 20 relative to the second member.

Preferably, rotational movement of the first member 20 relative to the second member (e.g. the button module 11) during dose delivery operation corresponds to a dose delivered during dose delivery operation. For example, the dose delivered may be proportional to an extent of rotational movement of the first member 20 relative to the button module 11 during the complete dose delivery operation. Especially if the dose delivered is large, the extent of rotational movement may comprise several complete revolutions (each 360°) of the first member 20 relative to the button module 11. Therefore, the sensor arrangement 120 should be ongoingly operated in the measurement state with high accuracy in order to correctly detect all revolutions.

The rotary sensor system 129 and especially the sensor arrangement 120 may be implemented in accordance to any one of the embodiments disclosed in WO 2019/101962 A1 and EP 20315066.9 (which are incorporated by reference), for example.

Preferably, the rotary sensor system 129 and especially the sensor arrangement 120 is/are implemented according to any one of the embodiments disclosed in EP 20315357.2. As noted above, said disclosure is incorporated by reference.

The electronic control unit 110 is configured to determine a size of the dose delivered during dose delivery operation based on the measurement data obtained from the sensor arrangement 120. In one embodiment, the electronic control unit 110 calculates the measurement result (i.e. the size of the dose delivered) based on the measurement data from the sensor arrangement 120. In another embodiment, the sensor arrangement 120 itself calculates the dose delivered and transmits the result to the electronic control unit 110. In the latter case, the electronic control unit 110 may simply determine the result of the sensor arrangement 120 the size of the dose delivered.

The memory unit 112 may be configured to cache position information or data on the relative angular position of the first member 20 and the button module 11, especially after completion of one dose delivery operation. Even if the power consumption of the electronic system 100 is reduced or if the electronic system 100 is switched off, this information may still be available for subsequent operations.

A power consumption of the sensor arrangement 120 and hence of the electronic system 100 may be particularly high while the electronic system 100 operates the sensor arrangement 120.

For example, with the sensor arrangement 120 having two electrically operated sensors 122A, 122B and one or two electrically operated source(s) for stimulating the sensors (for example the radiation emitters 121A, 121B), the power consumption of the electrical system 100 may be particularly high when the sensor arrangement 120 is operated.

Hence, power management with regard to the sensor arrangement 120 may have particular impact on the lifetime of the battery used as electrical power supply 150.

In one embodiment, in the context of normal dose delivery operation, the following sequence of events may occur and the electronic system 100 is adapted accordingly:

The button module 11 is depressed by at least the transition stroke.

The first component 20 starts to rotate relative to the button module 11 for the dose delivery operation, causing the rotary switch 230 to indicate said relative rotation (for example by providing the first signal).

The electronic control unit 110 switches the electronic system 100 to a measurement state based on said indication (first signal) from the rotary switch 230. In more detail, the main microcontroller 111 configures and starts the sensor controller 113 for operating the sensor arrangement 120 in the measurement state.

In the measurement state, the sensor controller 113 operates the sensor arrangement 120, for example the radiation emitter 121A, 121B and the optical sensors 122A, 122B thereof, at a high sampling rate to provide measurement data describing rotational movement of the first member 20 relative to the button module 11. Preferably, more than 100 samples per second are taken in the measurement state.

The dose is dispensed.

A dwell time may occur where there is no activity in the axial switch 220 and/or the rotary switch 230, and where the sensor arrangement 120, for example the optical sensors 122A, 112B thereof, detect no further relative rotational movement between first member 20 and button module 11.

When the axial switch 220 is finally released and/or when a time-out (of the measurement state) occurs, whereby no change of signals from the rotary switch 230 and the axial switch 220 occur for a period of time, this indicates that dose delivery operation has finished.

The electronic system 100, in particular the sensor controller 113, may store the measurement result regarding the dose delivered (dispensed) in the dose delivery operation and/or any error records.

The electronic system 100 switches out of the measurement state. The sensor controller 113 may be shut off. The electronic system 100 may automatically switch to the synchronization state if a new dose record is generated.

The electronic system 100 may be configured to perform one step, several steps, and/or all steps of any one of the methods 400, 500, 600, 700, and 800.

FIG. 3A schematically shows a modification of the electronic system 100 of FIG. 2. Naturally, the modified electronic system 100A may be configured to perform one step, several steps, and/or all steps of any one of the methods 400, 500, 600, 700, and 800 as well.

The modified electronic system 100A includes an electric use detector unit 200 connected to the electronic control unit 110, wherein the use detector unit 200 includes the axial switch 220 and the rotary switch 230. The use detector unit 200 may be a mechanical and/or electric sub-assembly comprising the axial switch 220 and the rotary switch 230. For example, the use detector unit 200 may be implemented according any one of the embodiments described in EP 20315451.3. The first signal of the axial switch 220 may be regarded as first signal of the detector unit 200. In a modification, the first signal of the axial switch 220 might be amplified, changed, transformed, filtered and/or digitized before it is transmitted to the electronic system.

In general, the axial switch 220 and the rotary switch 230 can be provided by a common switch assembly. In the modified electronic system 100A, the use detector unit 200 may comprise or consist of such a switch assembly.

Furthermore, FIG. 3A schematically shows a preferred structure of the electronic control unit 110 in more detail. The electronic control unit 110 includes the main microcontroller 111, the memory unit 112, the sensor controller 113, and a clock unit 114.

Preferably, the electronic control unit 110 is configured such that (only) the sensor controller 113 operates the sensor arrangement 120 in the measurement state. Additionally or alternatively, the electronic control unit 110 is configured such that (only) the main microcontroller 111 operates the sensor arrangement 120 in the failure detection functionality.

In one embodiment, the electronic control unit 110 is configured such that (only) the main microcontroller 111 controls operation of the electronic system 100, 100A in the failure detection functionality. Especially, the electronic control unit 110 may be configured such that (only) the main controller 111 controls operation of the electronic system 100, 100A in any state different from the measurement state.

Preferably, the sensor controller 113 is switched off (not operated) in the failure detection functionality. The electronic system 100, 100A, in particular the electronic control unit 110 may be configured such that the sensor controller 113 is switched off (not operated) in any state of the electronic system 100, 100A different from the measurement state.

The electronic control unit 110 may be configured such that the sensor controller 113 operates the sensor arrangement 120 with a high sampling rate in the measurement state, wherein the high sampling rate is at least 100 Hz. The sensor controller 113 may be configured to operate the sensor arrangement 120 with a higher sampling rate than the main microcontroller.

On the one hand, the higher sampling rate of the sensor controller 113 allows to provide measurement data with higher accuracy. Hence, the dose delivered using dose delivery operation can be determined more accurately based on measurement data obtained by the sensor controller 113. On the other hand, the operation of the sensor controller 113 may considerably increase the power consumption. Hence, the sensor controller 113 may be not operated if no high sampling rate is needed.

The memory unit 111 may be connected both to the main microcontroller 111 and the sensor controller 113.

In a preferred embodiment, the sensor controller 113 evaluates the measurement data. In particular, the sensor controller 113 calculates the dose delivered based on the measurement data. The sensor controller 113 may be configured to store the measurement data and/or the size of the dose delivered in the memory unit 113.

The clock unit 114 may be configured to provide a current point in time. Additionally, the clock unit 114 may provide at least a (first) timer. More preferably, the clock unit 114 provides a first timer and a second timer. In one embodiment, the clock unit 114 is part of the main microcontroller 111.

The sensor controller 113 may be an electronic component separate from the main microcontroller 111. The main microcontroller 111, the memory unit 112, and the sensor controller 113 may be fixed to a common PCBA. The clock unit 114, the communication unit 140 and/or the electrical power supply 150 (or a mount for the electrical power supply 150) may also be fixed to the common PCBA.

FIG. 3B schematically shows the combination of the electronic system 100A of FIG. 3A with the first member 20 of the dose setting and delivery mechanism 300. As noted above, the first member 20 may be the dial sleeve assembly of the dose setting and delivery mechanism 300 or a part of the dial sleeve assembly. Especially, the first member 20 may be the dial sleeve 302 as shown in FIG. 9.

An arrow 321 schematically illustrates a mechanical interaction between the first member 20 and the axial switch 220. An arrow 322 schematically illustrates a mechanical interaction between the first member 20 and the rotary switch 230.

In this embodiment, an encoder component 125 in the form of an encoder ring is axially and rotationally fixed to the first member 20 (which may be the dial sleeve 302). The sensor arrangement 120 and the encoder component 125 together form a motion sensor system (rotary sensor system 129).

An arrow 323 schematically illustrates an interaction between the sensor arrangement 120 and the encoder component 125. For example, one or more light emitters of the sensor arrangement 120 may emit light (which also may mean IR light and/or UV light) and the light may be reflected by the angularly separated detection regions of the encoder component 125. One or more sensors, preferably at least two optical sensors 122A, 122B of the sensor arrangement 120 may detect an increased reflection of electromagnetic waves if a detection region of the encoder component 125 faces the respective sensor 122A, 122B depending on the relative rotational position. The sensor arrangement 120 may provide the measurement data as Gray code data (explained below). Additionally or alternatively, the encoder component 125 may comprise angularly separated magnetic detection regions and the sensor arrangement 120 may comprise angularly separated magnetic field sensors, for example.

Methods for operating electronic systems like the electronic system 100, 100A are described with regard to FIGS. 4 to 8. Preferably, the electronic system 100, 100A is configured to perform one step, several steps, and/or all steps of any one of the methods described. In particular, the electronic control system 110 may be configured to control the electronic system 100, 100A to perform one step, several steps, and/or all steps of any one of the methods described.

The method (or operation) is started in step 401 ("Start axial switch monitoring").

The electronic system 100 has at least a first state and a failure detection functionality. The first state may be a sleep state. In the sleep state, the electronic system 100 may have no electrical power consumption or a low electrical power consumption. The electronic system 100 may be in the sleep state at step 401.

Step 402 ("Axial switch held activated?") includes checking whether the axial switch 220 is held activated. In order to decrease electrical power consumption, the electronic control unit 110 may be adapted to monitor (the state of) the axial switch 220 in the sleep state via interrupts and/or only periodically, for example at a time intervals in the range of 0.03 s to 0.5 s, for example each 0.05 or 0.1 s.

The electronic system 100 may be configured such that the sensor arrangement 120 is not operated (shut off) in the sleep state. In other words, the electronic control unit 110 may be configured not to operate the sensor arrangement 120 in the sleep state. This decreases the consumption of electrical power considerably. Hence, the electrical power supply 150 lasts for a longer time. This makes the electronic system 100 more reliable. In addition, the main microcontroller 111 may be in a sleep mode when the electronic system 100 is in the sleep state. In other words, the main microcontroller 111 may be at least partly switched off in the sleep state.

Step 402 comprises switching out of the sleep state, activating the failure detection functionality, and proceeding to step 441 when the axial switch 220 is held activated. For example, the electronic control unit 110 may be configured to switch the electronic system 100 out of the sleep state and to activate the failure detection functionality in response to the first signal. In particular, the electronic system 100 may be configured such that it wakes up and activates the failure detection functionality when the button module 11 is moved from its initial relative position to its activating relative position (range) whereas no second signal from the rotary switch 230 is received.

Preferably, the electronic system 100 is configured to switch out of the sleep state and to activate the failure detection functionality only when the axial switch 220 is (continuously) held activated for at least a predetermined time 'C' (see step 502 in FIGS. 5 to 8). In particular, the electronic system 100 may switch out of the sleep state and activate the failure detection functionality if the user presses the button module 11 distally towards the first member 20 and/or touches the cover 51 of the button module 11 for at least the time 'C'. The predetermined time 'C' may be a value in the range of 0.03 s to 0.3 s, for example 0.1 s. This reduces the risk that the failure detection functionality is activated by inadvertent operation of the button module 11. This helps to save electrical power.

The electronic control unit 110 may be configured to obtain a first point in time when activating failure detection functionality by the clock unit 114 and to store the first point in time in the memory unit 112. Additionally or alternatively, the electronic control unit 110 may be adapted to start a (first) timer when activating the failure detection functionality, for example by using the clock unit 114 and/or by counting processing cycles. The first point in time and/or the (first) timer may be used for determining of a time-out of the axial switch monitoring (see step 444).

Upon activation the failure detection functionality, information regarding an initial position of the first member 20 relative to the button module 11 may be obtained using the rotary sensor system 129. In particular, the electronic control unit 110 may be configured to operate the sensor arrangement 120 directly after activation of the failure detection functionality to obtain initial position data. The initial position data may be stored in the memory unit 112, for example. It can be user later for comparison with final position data.

However, preferably preceding position data stored in the memory unit 112 instead of (new) initial position data. The preceding position data indicates a latest determined position of the first member 20 relative to the button module 11 (or maybe a Dummy Value instead). Especially, the preceding position data may have been obtained after the end of the latest dose delivery operation and is still stored in the memory unit 112. Accordingly, in preferred embodiments, the electronic control unit hence does not operate the sensor arrangement 120 directly after activation failure detection functionality to obtain (new) initial position data but only relies on the preceding position data as described above.

The preceding position data may be also used in addition to initial position data.

Figure 4:
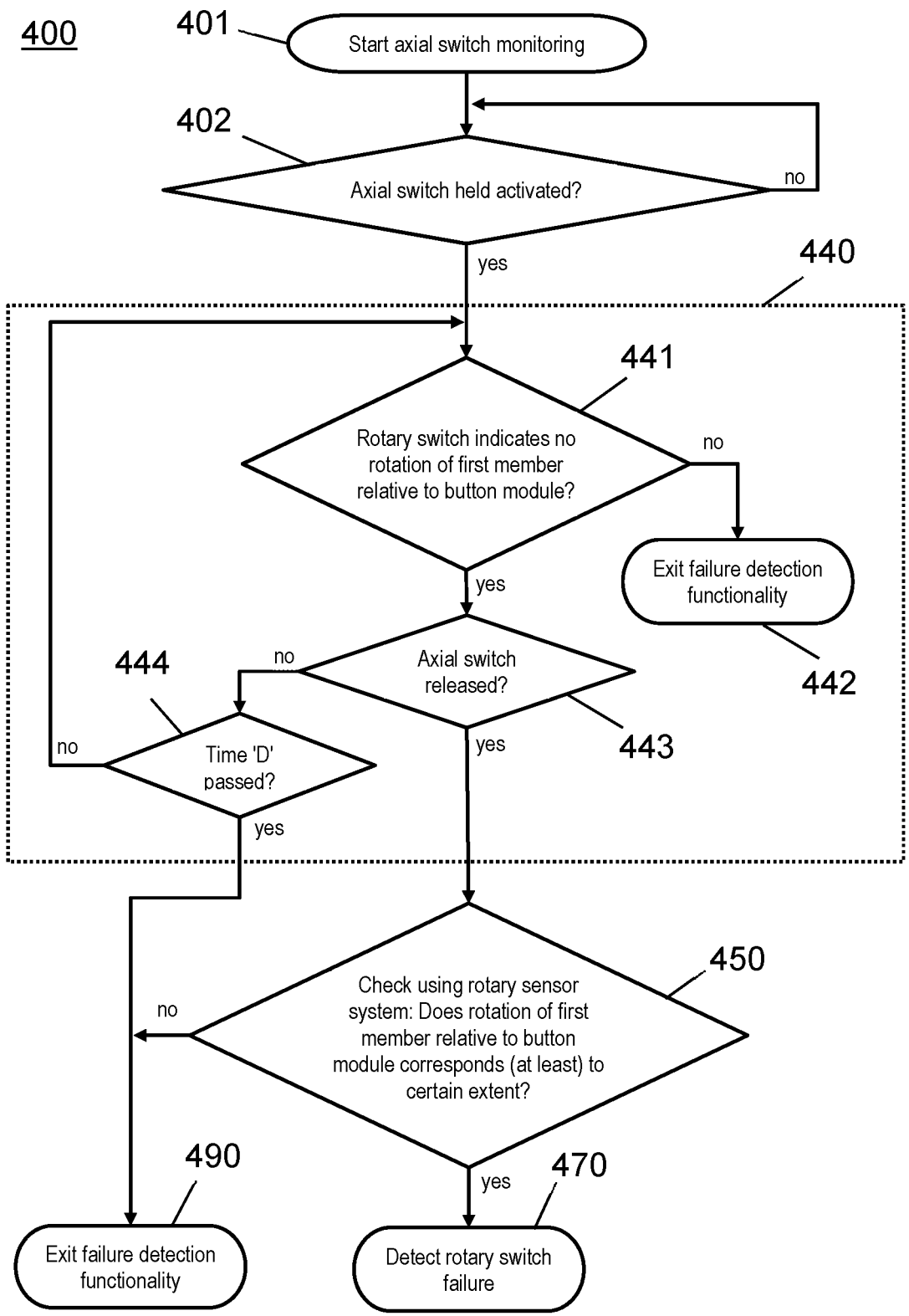
FIG. 4 shows a first method for operating the electronic systems of FIG. 2 and FIG. 3.

In FIG. 4, (at least) steps 441, 442, 443, 444, 450, 470, and 490 can be performed in the failure detection functionality, if applicable.

After switching to the failure detection functionality in step 402, step 441 may follow ("Rotary switch indicates no rotation of first member relative to button module?").

Step 441 comprises checking whether the rotary switch 230 indicates rotation of the first member 20 relative to the button module 11. For example, the electronic control unit 110 may be adapted to monitor the circuit state of the rotary switch 230. If the rotary switch 230 indicates said rotation, this proves that rotary switch 230 works correctly and that dose delivery operation has begun.

Method 400 comprises deactivating the failure detection functionality in case the rotary switch 230 indicates rotation of the first member 20 relative to the button module 11 (steps 441 and 442). In more detail, if the rotary switch 230 indicates rotation of the first member 20 relative to the button module 11 in step 441, operation proceeds to step 442 ("Exit failure detection functionality"). Step 442 may include switching the electronic system 100, 100A to the measurement state for determining the dose delivered by the dose delivery operation.

For example, switching of the rotary switch 230 between its broken circuit state and its closed circuit state may generate a signal of the rotary switch 230 (the second signal) and the electronic control unit 100 may be configured to switch the electronic system 100, 100A to the measurement in step 442 in response to the second signal.

Step 442 may include handing over control over (at least) the sensor arrangement 120 from the main microcontroller 111 to the sensor controller 113.

Measurement may be performed as described in WO 2019/101962 A1 and EP 20315066.9, and preferably as disclosed in EP 20315357.2 (all of which are incorporated by reference), for example.

Figure 6:
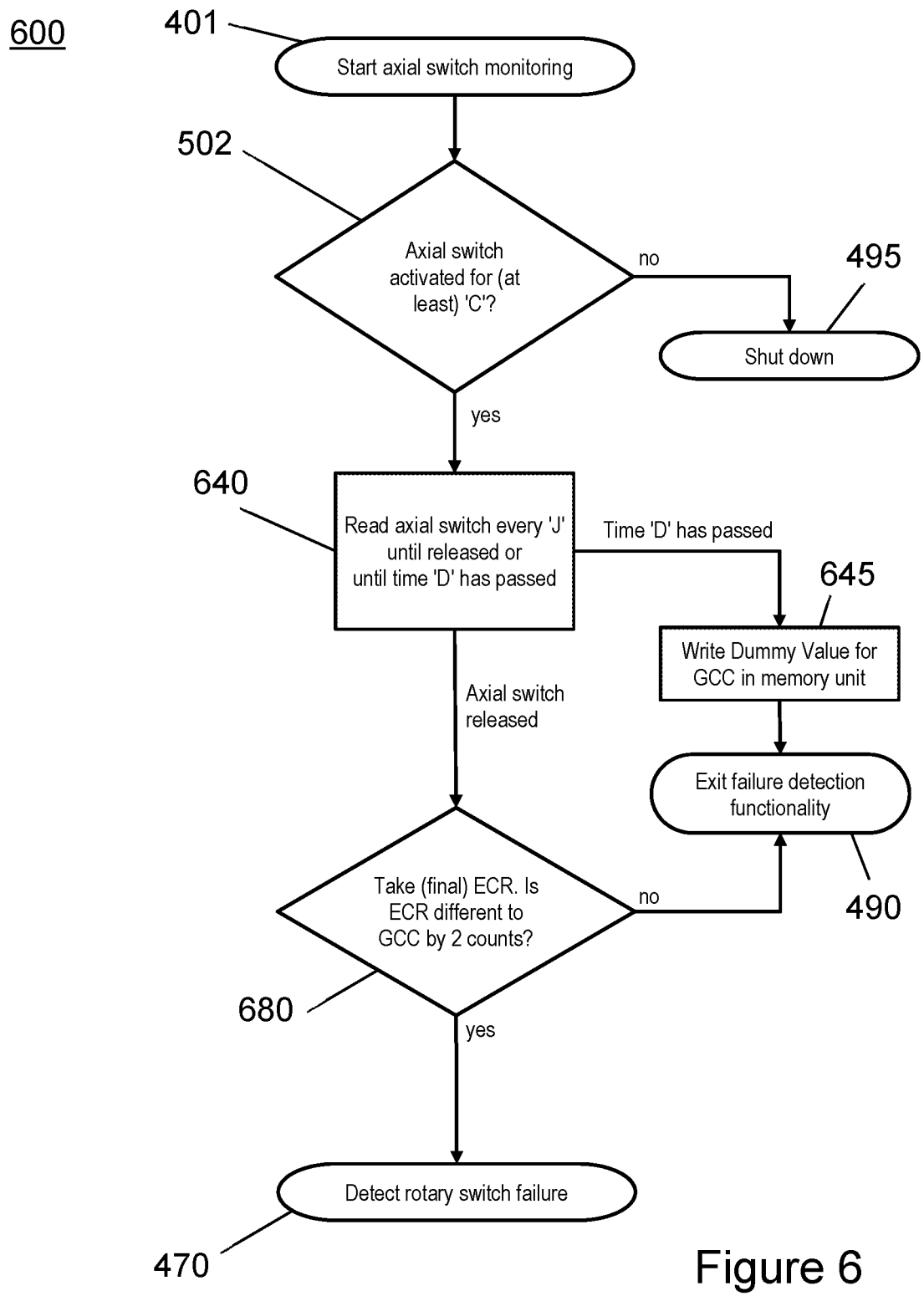
FIG. 6 shows a third method for operating the electronic systems of FIG. 2 and FIG. 3.

The electronic control system 100 may be configured to operate the sensor arrangement 120 in the measurement state with a measurement accuracy that is higher than in the failure detection functionality. The higher accuracy may be achieved by increasing the sampling rate, for example. This also encompasses cases in which there is no sampling rate in the failure detection functionality (i.e. the sampling rate is zero). It is noted that it is in general not necessary to operate the sensor arrangement 120 in the failure detection functionality periodically. For example, the sensor arrangement 120 might be operated only once in the failure detection functionality as shown in FIG. 4 and FIG. 6, respectively.

Preferably, the electronic control unit 110 is configured to operate the sensor arrangement 120 with a sampling rate of at least 100 Hz in the measurement state.

Additionally or alternatively, if the sensor arrangement 120 comprises more than one senor 122A, 112B and/or more than one radiation emitter 121A, 121B, a number of sensors 122A, 122B used in the second state and/or a number or radiation emitters 121A, 121B used in the measurement state may be higher than in the failure detection functionality.

The electronic system 100 may have an increased power consumption in the measurement state compared to the sleep state. The power consumption in the measurement state might be higher as in the failure detection functionality as well.

Figure 5:
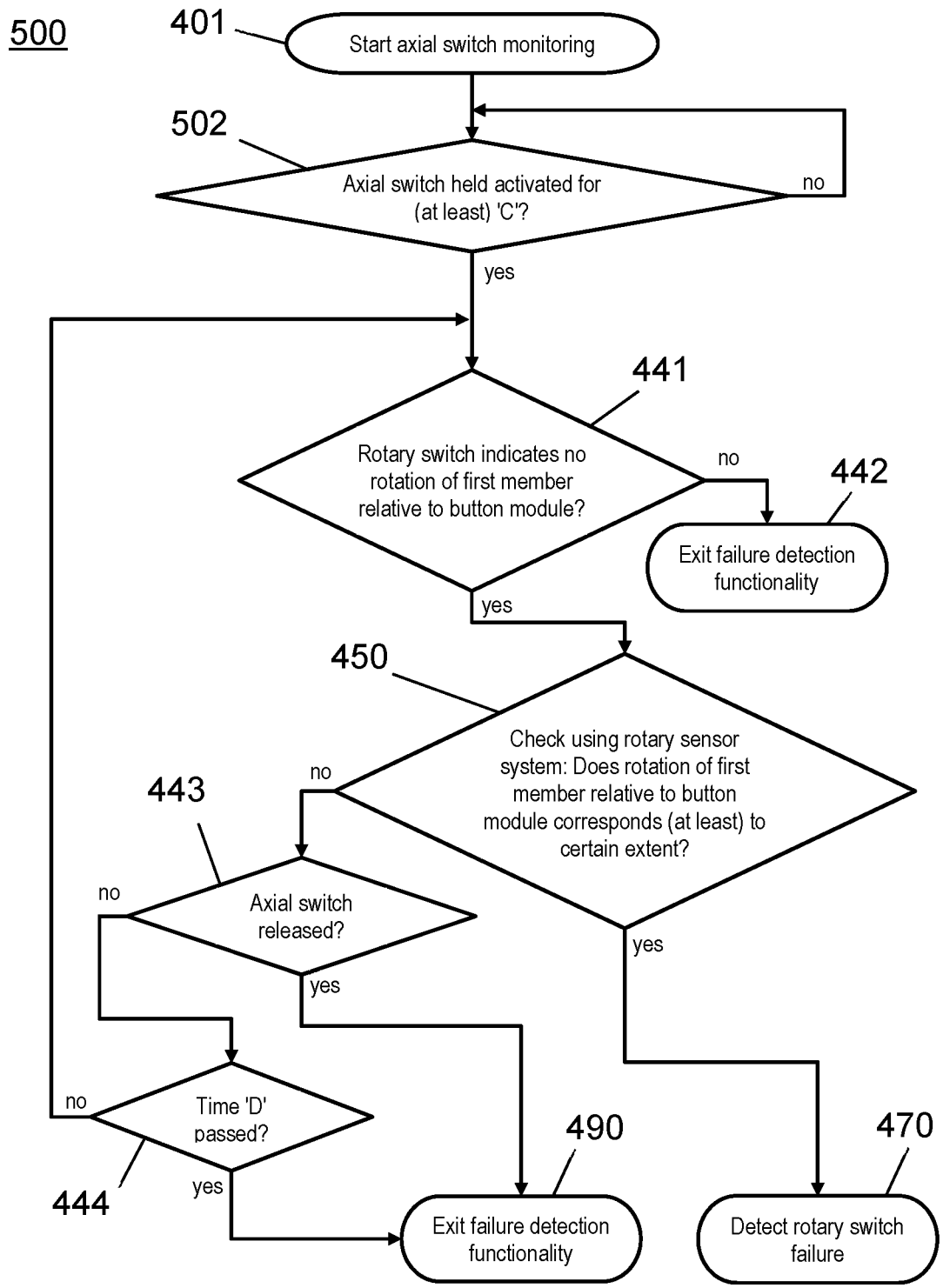
FIG. 5 shows a second method for operating the electronic systems of FIG. 2 and FIG. 3.

In FIGS. 4 and 5, it is checked only in step 441 whether rotary switch 230 indicates rotation of the first member 20 relative to the button module 11.

Preferably, the electronic control unit 110 ongoingly checks whether the rotary switch 230 indicates rotation of the first member 20 relative to the button module 11 while the electronic control unit 110 is in the failure detection functionality. For example, the signal of the rotary switch 230 (second signal) may be used as an interrupt signal. In this case, the electronic control unit 110 may deactivate the failure detection functionality and switch to the measurement state (step 442) when the rotary switch 230 indicates rotation of the first member 20 relative to the button module 11. This may be performed independently of which specific other step in the failure detection functionality is currently being performed.

Figure 7:
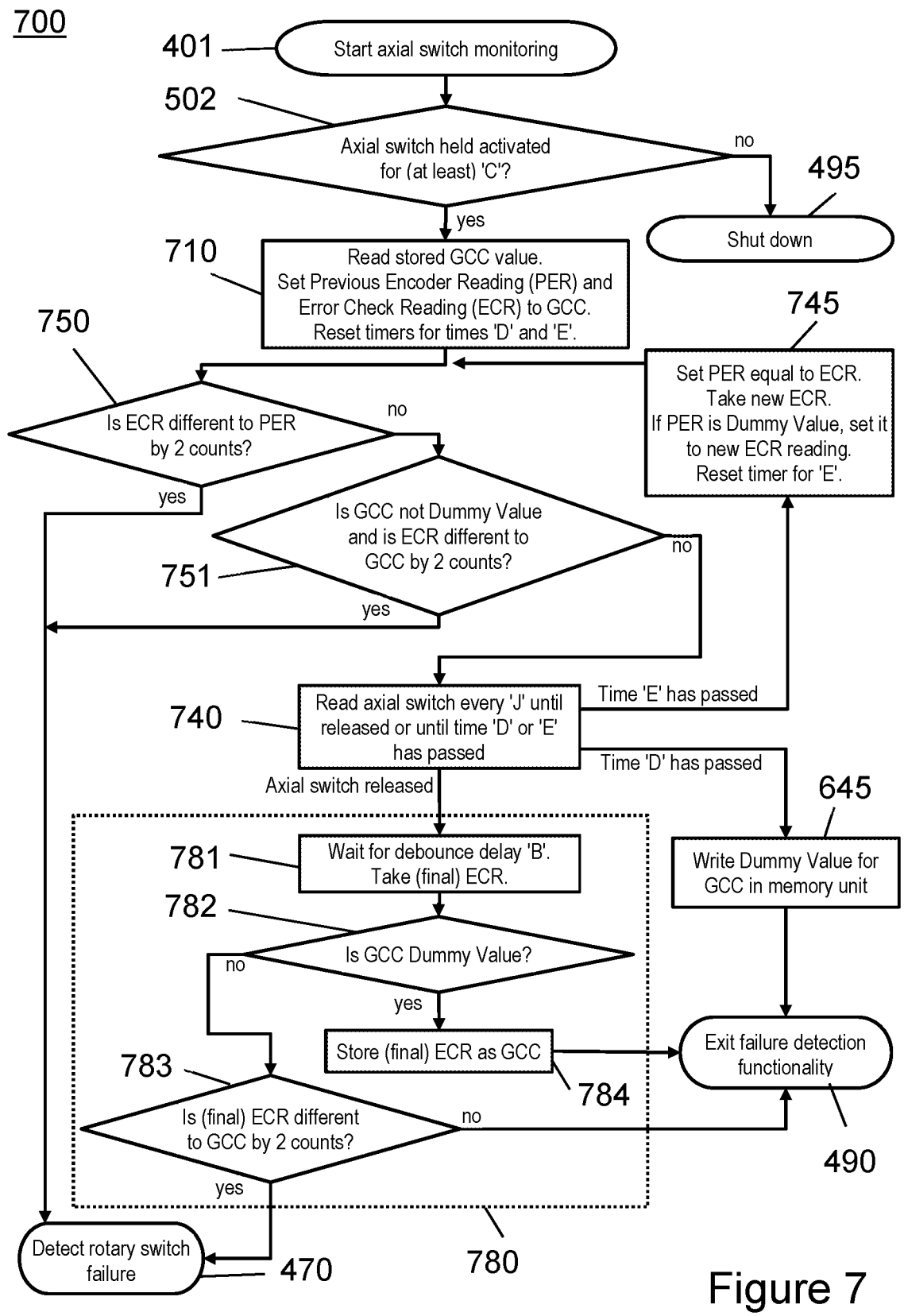
FIG. 7 shows a fourth method for operating the electronic systems of FIG. 2 and FIG. 3.

This applies with regard to method 600 shown in FIG. 6 and method 700 shown in FIG. 7. FIGS. 6 and 7 do not show step 441. Methods 400 and 500 may be modified accordingly as well. However, in other embodiments, step 640 in FIG. 6 and step 740 in FIG. 7 may be similar to step sequence 440 in FIG. 4 and include step 441 and, if applicable, step 442.

Turning back to FIG. 4, if the rotary switch 230 does not indicate (fails to indicate) rotation of the first member 20 relative to the button module 11 in step 441, the electronic control unit 110 proceeds to step 443 ("Axial switch released?").

Step 443 includes checking whether the axial switch 220 is (still) held activated. In a similar manner as explained above, the electronic control unit 110, in particular the main microcontroller 111, may monitor the axial switch 220 for that purpose.

If it is determined in step 443 that the axial switch 220 is still held activated, the operation proceeds with step 444 ("Time 'D' passed?"). Step 444 includes checking whether (at least) a time 'D' has passed since the activation of the failure detection functionality. Naturally, the term activation refers to the present instance of the failure detection functionality in this regard. The electronic unit 110 may perform this check, for example by comparing a current point of time with the first point of time stored in the memory unit 112.

Alternatively or additionally, the electronic unit 110 may use the (first) timer for the check in step 444.

The value of the time 'D' is preferably in the range from 10 s to 120 s, more preferably in the range from 30 s to 90 s. For example, the value for the time 'D' may be 20 s or 60 s. The dose delivery operation usually does not take longer than a few seconds.

If it is determined in step 444 that less than time 'D' has passed since the present activation of the failure detection functionality, the method 400 proceeds to step 441 again. As the electronic system 100 remains in the failure detection functionality, no new first point in time is stored and/or no new (first) timer is started.

If the period of time since the present activation of the failure detection functionality exceeds the predetermined threshold time 'D', the electronic control unit 110 proceeds to step 490 ("Exit failure detection functionality").

In step 490, the electronic control unit 110 may switch the electronic control system 100, 100A to another state. For example, the electronic control unit 110 may switch the electronic system 100, 100A to the synchronization state and/or the pairing state.

Additionally or alternatively, time-out of the axial switch 220 may be determined in step 490, for example by the electronic control unit 110. If time-out is determined, it is preferably necessary that the axial switch 220 must be released and/or that at least a predetermined period of time ('dead time') must pass after step 490 before the electronic system 100, 100A is allowed to switch to the failure detection functionality again, for example from the sleep state. The electronic control system 110 may switch the electronic system 100, 100 to the sleep state in step 490.

It may occur that the button module 11 is continuously but inadvertently kept in its activating relative position (range), for example in case the drug delivery device 1 is squeezed along the axial direction in a pocket or a bag or between two objects. Accordingly, the axial switch 220 is held in its activating state. Implementation of step 444 (and step 490) prevents that the failure detection functionality remains ongoingly activated for a long time and drains the electrical power supply 150 in such a case.

If it is determined in step 444 that the axial switch 220 is no longer in its activating state, the operation proceeds to step 450 ("Rotary switch indicates that rotation of first member relative to button module corresponds to (at least) a predetermined extent?").

Step 450 comprises checking whether a rotation of the first member 20 relative to button module 11 in the failure detection functionality corresponds to (at least) a certain extent using the rotary sensor system 129 (in more detail by operating the sensor arrangement 120 of the latter).

In particular, the electronic control unit 110 may operate the sensor arrangement 120 of the rotary sensor system 129 to obtain measurement data indicative of a final (rotational) position of the of the first member 20 relative to the button module 11 (final position data). The final position may be stored, for example in the memory unit 112. It may be used as preceding position data in a next instance of the failure detection functionality, if applicable.

The electronic control unit 110 may compare the final position data with the preceding position data (and/or the initial position data) in order to determine whether an extent of a rotation of the first member 20 relative to the button module 11 corresponds to (at least) a certain extent (predetermined extent). If no such relative rotation occurred, the extent is obviously zero.

As pointed out above, the electronic system 100 may be adapted to store position data indicating the rotational position of the first member 20 relative to the button module 11 after the end of each dose delivery operation as preceding position data, for example in the memory unit 112. Final position data of a preceding instance of the failure detection functionality may be used as well or instead for the comparison if no dose delivery operation occurred between the preceding instance and the present instance of the failure detection functionality.

If the rotation of the first member 20 relative to button module 11 in the failure detection functionality corresponds to (at least) the certain extent, failure of the rotary switch 230 is detected (step 470). Especially, the electronic control unit 110 may be configured to determine the failure of the rotary switch 230 at least in this case. The electronic control unit 110 may be configured to switch to a failure detected mode and/or to provide a failure indication. For example, the electronic control unit 110 may store a failure indication in the memory unit 112. The electronic system 100 may stop at the end of step 470.

Preferably, the certain extent has a predetermined value that is greater than zero. The certain extent may correspond to a predetermined angle and/or a predetermined dose amount, for example a predetermined fraction of one unit of insulin.

The certain extent may be estimated from mechanical variations and/or tolerances. In particular, the certain extent may be estimated from mechanical variations and/or tolerances within the dose setting and drive mechanism 300 and/or the button module 11. For example, the first member 20 may be able to rotate relative to the button module 11 by a certain angle at the maximum even when the first member 20 is rotationally coupled to the button module by the clutch. The certain extent may correspond to the certain angle or to an extent that is larger than the certain angle. For example, the certain extent may correspond to at least 1.1 times the certain angle. In this way, a risk that the electronic control unit 110 determines failure of the rotary switch 230 incorrectly is reduced.

In a modification not shown in the drawings, it is instead checked whether the rotation in the failure detection functionality exceeds the certain extent. In this case, the certain extent may be zero. This means, any relative rotation detected in step 450 by using the rotary sensor system 129 will lead to determining failure of the rotary switch 230.

If the rotation of the first member 20 relative to button module 11 in the failure detection functionality determined using the rotary sensor system 129 corresponds to (at least) the certain extent (or in the modification: exceeds the certain extent), this shows that the rotary switch 230 suffers from failure. The rotary switch 230 should have indicated the rotation in the failure detection functionality in step 441 before (or by at least one corresponding interrupt). As this did not happen, there must be a failure regarding the rotary switch 230.

Alternatively, the check in step 450 exhibits that the rotation of the first member 20 relative to button module 11 in the failure detection functionality does not correspond to (at least) the certain extent (or in the modification: does not exceed the certain extent) and the operation proceeds to step 490 ("Exit failure detection functionality"). In step 490, the electronic control unit 110 may switch the electronic system 100, 100A to a different state, for example to the sleep state, the synchronization state, or the paring state. It may depend on a duration for how long the axial switch 220 has been (continuously) held before the present release to which state the electronic system 100, 100 is switched.

Summed up, the rotary sensor system 129 is used to check, in the failure detection functionality, whether a relative rotation between the first member 20 and the button module 11 occurs, which corresponds to (at least) the certain extent (in the modification: exceeds the certain extent) although the rotary switch 230 does not indicate any relative rotation.

As noted above, the electronic control unit 110 may be adapted to switch to the measurement state in response to the signal from the rotary switch 230 (second signal) indicating relative rotation between the first member 20 and the button module 11.

If the rotary switch 230 does not work properly, the electronic system 100 might not be switched to the measurement state at all.

In an even worse case, the electronic system 100 is switched to the measurement state but too late. Consequently, there is a risk that wrong measurement results regarding doses delivered are determined. It is possible that a measurement result indicates a smaller dose than it was actually dispensed. This could severely impair a patient's health. For example, if patient injects a desired dose of insulin but the electronic system incorrectly indicates that only a smaller dose was dispensed, the patient might start another dose delivery operation in order to add the difference. This might result in an unintentional overdose and eventually in a very dangerous hypoglycemic state of the patient. The present invention helps to avoid such risks by checking whether the rotary switch 230 works properly.

It is envisaged that the electronic control unit 110 may be configured to determine failure of the axial switch 220 if the state of the rotary switch 230 is changed without a corresponding change of the state of the axial switch 220 in embodiments where at least completing dose delivery operation requires activation of the axial switch 220 (in case the axial switch 220 works properly).

Method 500 shown in FIG. 5 is a modification of method 400 shown in FIG. 4. Only the differences to method 400 are discussed in detail. Apart from that, method 500 corresponds to method 400 and the same modifications and advantages apply accordingly.

As explained above, in step 502, activation of the failure detection functionality occurs only when the axial switch 220 is (continuously) held activated for at least the predetermined time 'C'. In other words, predetermined time 'C' may be a minimum time for which the button module 11 must be pressed and/or touched by the user for activation of the failure detection functionality (pre-defined user input).

In method 500, (at least) steps 441, 442, 450, 443, 444, 470, and 490 can be performed in the failure detection functionality.

One major difference between method 400 and method 500 concerns step 450 ("Check using rotary sensor system: Does rotation of first member relative to button module corresponds (at least) to certain extent?"). In method 400, step 450 is only performed if step 443 exhibits that the axial switch is released (no longer held activated). Hence, step 450 is performed only once at the maximum each time the electronic system 100 is in the failure detection functionality, respectively. This saves energy because the sensor arrangement 120 is operated only once at the maximum for step 450 each time the electronic system 100 is in the failure detection functionality as well.

In method 500, step 450 is performed repeatedly in the failure detection functionality while the axial switch 220 is still held activated (not released). In this example, step 450 is performed before step 443.

In the exemplary method 500, the operation proceeds from step 441 ("Rotary switch indicates no rotation of first member relative to button module?") directly to step 450 if the rotary switch 230 does not indicate (fails to indicate) rotation of the first member 20 relative to the button module 11 in step 441. Hence, even in case the axial switch 220 is not (yet) released, step 450 will be performed.

Instead, method 500 proceeds from step 450 to step 443 ("Axial switch released?") if step 450 exhibits that the rotation of the first member 20 relative to button module 11 (determined using the rotary sensor system 129) does not correspond to (at least) the certain extent (in a modification: exceeds the certain extent).

In method 500, the rotary sensor system 129 is used periodically in the failure detection functionality for the check according to step 450. Accordingly, the electronic control unit 110 may be configured to operate the sensor arrangement 120 with a (low) sampling rate in the failure detection functionality. The (low) sampling rate in the failure detection functionality is preferably in the range from 0.2 Hz to 5 Hz, for example 1 Hz. The use of such a low sampling rate may not allow a measurement result regarding the dose delivered during dose delivery operation to be properly determined.

As noted above, the sampling rate in the measurement state may be higher than the sampling rate in the failure detection functionality. Preferably, the sensor arrangement 120 is operated by the main microcontroller 111 in the failure detection functionality but by the sensor controller 113 in the measurement state. By this, electrical power consumption is reduced in the failure detection functionality.

If step 450 exhibits that the rotation of the first member 20 relative to button module 11 determined using the rotary sensor system 129 corresponds to (at least) the certain extent, the operation proceeds to step 470 ("Detect rotary switch failure").

Step 470 may include determining failure of the rotary switch 230, changing the electronic system 100 to another state (for example a failure state), and/or providing a failure alert. The failure alert may indicate (possible) failure of rotary switch 230. Providing the failure alert may include generating a failure indicating signal, and preferably transmitting the failure indicating signal by means of the communication unit 140 and/or
presenting a visual, audible, and/or tangible alert to a user.

As in method 400, the operation according to method 500 proceeds from step 443 to step 444 ("Time 'D' passed?") if it is determined in step 443 that the axial switch 220 is not released (hence still held activated).

In method 500, steps 441, 450, 443, and 444 constitute a "monitoring loop". The "monitoring loop" is repeated as long the operation does not proceed to any of the steps 442, 470, and 490.

The electronic control unit 110 (in particular the main microcontroller 111) may be configured to monitor the rotary switch 230 with a monitoring rate (at least) in the failure detection functionality. The monitoring rate for the rotary switch 230 in the failure detection functionality may be the same as the monitoring rate of the axial switch 220 in the failure detection functionality or may differ from the latter.

As noted above, the electronic control unit 110, especially the main microcontroller 111 may be configured to monitor the axial switch 220 in the first state and/or in the failure detection functionality. A monitoring rate for the axial switch 220 in the failure detection functionality may be higher than the sampling rate in the failure detection functionality, preferably at least twice the latter, more preferably at least five times the latter.

For example, the electronic control unit 110 may perform step 450 between steps 441 and 443 only every fifth repetition of the monitoring loop of method 500. In the respective four intervening repetitions, step 450 may be simply skipped in order to decrease the electrical power consumption.

Alternatively, a (second) timer may be used to determine whether step 450 is performed in a respective instance of the monitoring loop. This corresponds to the approach in method 700 shown in FIG. 7. The (second) timer may be set back each time when step 450 is performed in this case.

In preferred embodiments, the sensor arrangement 120 is configured to produce or form a Gray code (at least when operated in combination with the encoder component 125). The Gray code may uniquely identify successive relative angular positions. For example, corresponding embodiments are explained in detail in WO2021191327 and WO2021191322, which are incorporated by reference.

A sequence of successive relative angular positions between the first member 20 and the button module 11 may be identifiable via the Gray code data. Particularly, data on two subsequent positions may differ in only one bit.

In more detail, the sensor arrangement 120 may comprise two sensors 122A and 122B. When the first member 20 (for example the dial sleeve assembly) rotates during dose delivery operation relative to the button module 11, for example anti-clockwise, the two sensors 122A and 122B may produce 2-bit Gray code outputs (11, 01, 00, 10). The 2-bit code sequence repeats every four units dispensed. As an example, the four possible outputs may be simply indicated by the values 0, 1, 2, 3. During relative rotation, the Gray code output (and hence the corresponding Gray code values) may repeat after each one-sixth revolution, for example.

As an example, the sensor arrangement 120 may provide the same Gray code value '0' when the rotational position of the first member 20 relative to the button module 11 is in the following relative angular position ranges: 1° to 15°, 61° to 75°, 121° to 135°, 181° to 195°, 241° to 255° and 301° to 315; and the Gray code value '1' is provided when the rotational position of the first member 20 relative to the button module 11 is in the following relative angular position ranges: 16° to 30°, 76° to 90°, 136° to 150°, 196° to 210°, 256° to 270°, and 316° to 330°. Accordingly the, Gray code value '2' is provided for six other relative angular position ranges and the Gray code value '3' is provided for further six other relative angular position ranges.

Naturally, a Gray code resolution can be enhanced easily if more than two sensors 122A, 122B are used.

This coded output facilitates the detection of positive (anticlockwise) and negative (clockwise) rotations. For example, when the sensor arrangement reads '11' a change to '01' would be a positive rotation and the change to '10' would be a negative rotation. This directionally sensitive system has advantages over a purely incremental system, in the ability to accurately determine true dispensed dose volume in the cases where negative rotations can occur. For example, the first member 20 of the dose setting and drive mechanism 300 may tend to over-rotate at the end of dose delivery operation before 'backing-off' when the user releases the button module 11.

In an embodiment using the device disclosed in EP 2 890 435, two optical sensors may be used. The Gray code caching resolution with this system is limited to 4 discrete sensor states, such that there is a 1 in 4 chance that a change in rotational position would not be detected if this mitigation was used in isolation.

The electronic system 100, 100A stores position data indicative of the position of the first member 20 (e.g. the dial sleeve assembly) relative to the second member (e.g. the button module 11) directly after the end of dose delivery operation. As described below, this position data can be compared later with new position data, for example in a later instance of the failure detection functionality as preceding position data.

More specifically, the electronic system 100, 100A may be adapted to store Gray code data corresponding to an encoder reading taken each time directly after dose delivery operation has ended, for example before the electronic system 100, 100A switches out of the measurement state. Said (preceding) Gray code data may be referred to as GCC in the following. The electronic system 100, 100A may be configured to store the GCC in the memory unit 112, for example.

The term "encoder reading" may denote position data provided by the sensor arrangement 120 for a single position.

The electronic system 100, 100A may be also configured to further store position data (e.g. in the form of Gray code data) obtained from the sensor arrangement 120 as an error check encoder reading (also referred to as ECR), for example while the failure detection functionality is active. The ECR may be stored in the memory unit 112.

Additionally, the electronic system 100, 100A may be configured to further store position data (e.g. in the form of Gray code data) as a previously-taken encoder reading (also referred to as PER), for example in the memory unit 112. For example, the PER may be set equal to a preceding ECR if a new ECR is stored.

According to a further aspect, the electronic system 100, 100A may be configured to store a "Dummy Value". The Dummy Value is specific data, such as a specific value, that indicates that a valid GCC could not be taken. For example, the electronic system 100, 100A may be adapted to store the Dummy Value as the GCC if no valid encoder reading can be taken after the end of dose delivery operation. The Dummy Value may correspond to impossible Gray code data.

Method 600 shown in FIG. 6 and method 700 shown in FIG. 7 are more detailed examples for operating the electronic system 100, 100A in embodiments using stored Gray code data.

In general, both methods 600 and 700 include checking, in the failure detection functionality, whether both
a Gray change of 2 counts occurs while the axial switch 220 is kept in its activating state and
the rotary switch 230 does not indicate relative rotation of the first member 20 (e.g. the dial sleeve assembly) relative to the button module 11.

If both conditions are fulfilled, failure of the rotary switch 230 is determined (see step 470 in FIGS. 6 and 7).

The above embodiment, in which the Gray code repeats every 4 counts, is considered as a non-limiting example. The values 0, 1, 2, 3 may be valid Gray code values (Gray code data) in such an embodiment. The Dummy Value could be 5 in this embodiment, for example.

Mechanical variances and tolerances may give rise to Gray code changes up to 1 in either direction. Therefore, failure of the rotary switch 230 is not determined in case the final position data obtained by the sensor arrangement differs from the preceding position data (and/or the initial position data) by any one of +1 count or −1 count.

In addition, consider that anti-clockwise rotation of the first member 20 relative to the button module 11 during dose delivery operation by a specific extent may correspond to a dispense of one unit of insulin. Further, anti-clockwise rotation of the first member 20 relative to the button module 11 by said extent may corresponds to an increase of the Gray code value by 1 count (an increase of 1 count in Gray code value corresponds to one unit of insulin delivered). If anti-clockwise rotation starts from an initial relative rotational position corresponding to Gray code value 2, the new Gray code after said rotation is 3=[2+1] mod 4. Anti-clockwise rotation corresponding to delivery of three units of insulin (change in Gray code value: +3 counts) starting from the same initial rotational position (Gray code value 2) results in a new Gray code of 1=[2+3] mod 4. However, clockwise rotation corresponding to −1 unit of insulin (change in Gray code value: −1 counts) from the same initial position (Gray code value 2) results in the same new Gray code value of 1=[3−1] mod 4. Hence, a change of Gray code value of +3 counts cannot be distinguished from a Gray code change of −1 count in this example.

In such an embodiment, only a Gray code change of exactly 2 (+2 counts or minus 2 counts) may reliably indicate failure of the rotary switch 230.

In a preferred embodiment, the variances and tolerances give rise only to a Gray code change of +1. Therefore, failure of the rotary switch 230 is determined in case that the final position data obtained by the sensor arrangement differs from the preceding position data (and/or the initial position data) by a value different from 0 count and −1 count.

More preferably, the mechanical variances and tolerances are so small that they can be neglected. Then, failure of the rotary switch 230 is determined in case of any difference between the final position data and the preceding position data (and/or the initial position data). In other words, as described elsewhere in this disclosure, the certain extent is zero and failure of the rotary switch 230 is determined in case that the extent of the specific movement (here: the rotation) of the first member 20 relative to the second member in the failure detection functionality exceeds (is different from) zero.

It is evident that this can be different for other embodiments employing more sensors 122A, 122B and more valid Gray code values (see EP 20315357.2 incorporated by reference).

Turning back to the method 600 in FIG. 6, only the differences to methods 400 and 500 are described in detail. Apart from that, method 600 corresponds to method 400 and 500. The same modifications and advantages are applicable accordingly.

Method 600 comprises continuous monitoring of the rotary switch 230, at least within the failure detection functionality, for example by at least one interrupt. As noted above, the monitoring rate for the rotary switch 230 in the failure detection functionality may be the same as the monitoring rate of the axial switch 220 in the failure detection functionality or may differ from the latter. As soon as the rotary switch 230 indicates rotation of the first member 20 relative to the button module 11, the electronic system 100, 100A may switch to the second state (measurement state).

The operation is started in step 401 ("Start axial switch monitoring") and proceeds to step 502.

Step 502 includes checking whether the axial switch 220 is kept in the activating state for at least the predetermined time 'C'.

If this is not the case, the electronic system 100 proceeds to step 495 ("Shutdown"). The electronic unit 110 may be configured to switch the electronic system 100, 100A back into the sleep state in this case.

In a similar manner as described with regard to step 402 in FIG. 4, step 502 may comprise storing the first point in time at which activation of the failure detection functionality occurs, for example by using the clock unit 114 and the memory unit 112. Additionally or alternatively, step 502 may comprise starting the (first) timer when activating the failure detection functionality, for example by using the clock unit 114 and/or by counting processing cycles. The first point in time and/or the (first) timer may be used for determining in step 640 whether the time 'D' has passed since switching from the activation of the failure detection functionality.

In method 600, (at least) steps 640, 680, 645, 470, and 490 can be performed in the failure detection functionality.

If it is determined in step 502 that the axial switch 220 is held activated for at least the predetermined time 'C', the operation proceeds to step 640 ("Read axial switch every 'J' until released or until time 'D' has passed").

Step 640 comprises monitoring the axial switch 220 at time intervals 'J'. In other words, the axial switch 220 is monitored with the monitoring rate 1/'J'. The time intervals 'J' may be in the range from 0.01 s to 1 s. For example, the time intervals 'J' may be 0.05 s. It is checked whether the axial switch 220 is still activated. This may correspond to step 443 in FIG. 4.

In addition, step 640 includes monitoring whether (at least) the time 'D' has passed since last switching from the first mode to the failure detection functionality. This may correspond to step 444 in FIG. 4 and FIG. 5.

If it is determined in step 640 that time 'D' has passed since last switching from the first mode to the failure detection functionality, the operation proceeds from step 640 to step 645 ("Write Dummy Value for GCC in memory unit") and further to step 490 ("Exit failure detection functionality").

Step 645 includes writing the Dummy Value as GCC in the memory unit 112. In more detail, the electronic control unit 110 may be configured to store the Dummy Value as GCC in the memory unit 112 in this case. Storing the Dummy Value as GCC may prevent a comparison occurring the next time.

If it is determined in step 640 that that the axial switch 220 is released (before time 'D' has passed since the activation of the failure detection functionality), operation proceeds to step 680 ("Take (final) ECR reading. Is ECR different to GCC by 2 counts?").

Step 680 may include waiting for a (predetermined) time delay at the beginning of step 680, hence before any further operations of step 680 start ("debounce delay"). The debounce delay is explained in more detail with regard to step 781 of FIG. 7 below.

Step 680 comprise taking an ECR, for example using the rotary sensor system 129. In particular, the main microcontroller 111 may operate the sensor arrangement 120 to provide new Gray Code data. Step 680 further includes comparing whether the ECR is different from the stored GCC by (at least) the certain extent. In case of the exemplary embodiment presented above, step 680 includes checking whether the ECR is different from the GCC by 2 counts. In other embodiments, step 680 may include checking whether the ECR differs from the GCC by another predetermined value,
by any one of a plurality of predetermined values,
by at least a predetermined value, or
by more than a predetermined value.

The latest case also includes the case of checking whether the ECR differs from the GCC at all (i.e. the difference is not zero, i.e. larger than zero).

The method may provide an additional step of taking and storing a GCC when the electronic system 100 is switched into the first state by using the rotary sensor system 129 (i.e. by operating the sensor arrangement 120), at least when the electronic system 100 is switched into the first state after dose delivery operation ended. In this regard, the GCC then may be used as preceding position data later.

If the result in step 680 is 'yes', the operation proceeds to step 470 ("Detect rotary switch failure") explained above with regard to FIG. 4.

If the result in step 680 is 'no', the operation may proceed to step 490 ("Exit failure detection functionality").

In method 600 shown in FIG. 6, step 680 is only performed once at the maximum for each time the electronic system 100 is switched to the failure detection functionality. In more detail, step 680 is only performed if the axial switch 220 is released in the failure detection functionality before time 'D' has passed. In this regard, method 600 is similar to method 400 shown in FIG. 4.

Step 680 might be replaced by step sequence 780 shown in FIG. 7.

In FIG. 6, the monitoring loop of the failure detection functionality consists of or comprises step 640. Step 640 may be similar to or the same as the step sequence 440 in method 400 (shown in FIG. 4).

Regarding method 700 shown in FIG. 7, only the differences to method 600 are described in detail. Apart from that, method 700 corresponds to method 600 (and hence to methods 400 and/or method 500 as this is true for method 600). The same modifications and advantages are applicable accordingly.

In method 700, (at least) steps 710, 740, 745, 750, 751, 781, 782, 783, 784, 645, 470, and 490 can be performed in the failure detection functionality.

In FIG. 7, the monitoring loop of the failure detection functionality consists of steps 750, 751, 740, and 745.

Method 700 differs from method 600 in checking whether rotation of the first member 20 relative to button module 11 corresponds to the certain extent additionally within the monitoring loop (see steps 750 and 751).

If it is determined in step 502 that the axial switch 220 is held in the activating state for at least the predetermined time 'C', the operation proceeds to step 710 ("Read stored GCC value. Set Previous Encoder Reading (PER) and Error Check Reading (ECR) to GCC. Reset timers for times 'D' and 'E'.").

In method 700, step 502 and/or step 710 may comprise storing the first point in time of activating the failure detection functionality, for example by using the clock unit 114 and the memory unit 112. Additionally or alternatively, step 502 and/or 710 may comprise starting the (first) timer when activating the failure detection functionality, for example by using the clock unit 114 and/or by counting processing cycles. The first point in time and/or the (first) timer may be used for determining in step 740 whether the time 'D' has passed since the activation of the failure detection functionality.

Similarly, step 502 and/or step 710 may comprise storing the point of time of activating the failure detection functionality occurs as a (second) point in time, for example by using the clock unit 114 and the memory unit 112. Additionally or alternatively, step 502 and/or step 710 may comprise starting the (second) timer activating the failure detection functionality, for example by using the clock unit 114 and/or by counting processing cycles. The second point in time and/or the (second) timer may be used for determining in step 740 whether the time 'E' has passed since the activation of the failure detection functionality and hence since entering the monitoring loop.

Step 710 comprises reading the stored GCC. As in method 600, the GCC is the preceding position data. The GCC may be stored in the memory unit 112, for example. Step 710 further includes setting the PER and the ECR to the GCC. Hence, both the PER and the ECR correspond to the GCC when the monitoring loop is entered.

After step 710, the operation proceeds to step 750 ("Is ECR different to PER by 2 counts?").

Step 750 includes comparing whether the ECR differs from the stored PER by (at least) a (second) certain extent. In case of the exemplary embodiment presented above, the (second) certain extent of step 750 is 2 counts. In other embodiments, step 750 may include checking whether the ECR differs from the PER
- by another predetermined value,
- by any one of a plurality of predetermined values,
- by at least a predetermined value, or
- by more than a predetermined value.

If the result in step 750 is 'yes', the operation may proceed to step 470 ("Detect rotary switch failure"), which is explained above with regard to FIG. 4.

If the result in step 750 is 'no', the operation proceeds to step 751 ("Is GCC not Dummy Value and is ECR different to GCC by 2 counts?"). Naturally, when performing step 750 directly after step 710, the result will be 'no' as both the PER and ECR were set to GCC in step 710.

Step 751 includes comparing whether the ECR differs from the stored GCC by (at least) a (third) certain extent. In case of the exemplary embodiment presented above, the (third) certain extent of step 751 is the (same as the second) certain extent of step 750, namely 2 counts. In other embodiments, step 751 may include checking whether the ECR differs from the PER
- by another predetermined value,
- by any one of a plurality of predetermined values,
- by at least a predetermined value, or
- by more than a predetermined value.

In other words, the second certain extent and the third certain extent may be the same or different.

No comparison of the ECR with the GCC is made if the GCC corresponds to the Dummy Value. For this, step 751 includes checking whether the GCC corresponds to the Dummy Value.

If the result in step 751 is 'yes', the operation may proceed to step 470 ("Detect rotary switch failure"), which is explained above with regard to FIG. 4.

If the result in step 751 is 'no', the operation proceeds to step 740 ("Read axial switch every 'J' until released or until time 'D' or 'E' has passed"). Naturally, when performing steps 750 and 751 directly after step 710, the result will be 'no' as both the PER and ECR were set to GCC in step 710.

Like step 640, step 740 includes monitoring the axial switch 220 at time intervals 'J' and monitoring whether (at least) the time 'D' has passed since last switching from the first mode to the failure detection functionality.

In other words, the axial switch 220 is monitored with the monitoring rate 1/'J' like in step 640. Step 740 constitutes a high frequency sub-loop for axial switch monitoring within the monitoring loop.

Similar as in method 600, the operation proceeds from step 740 to step 645 ("Write Dummy Value for GVV in memory unit") and further to step 490 ("Exit failure detection functionality") if it is determined in step 740 that time 'D' has passed since last switching from the first mode to the failure detection functionality.

If it is determined in step 740 that that the axial switch 220 is released (before time 'D' has passed since the activation of the failure detection functionality), operation proceeds from step 740 to step sequence 780. Step sequence 780 is similar to step 680 in FIG. 6 but more detailed. In this embodiment, step sequence 780 includes steps 781, 782, 783, and 784.

Step sequence 780 starts with step 781 ("Wait for debounce delay 'B'. Take (final) ECR"). Step 781 include waiting for a (predetermined) time delay 'B' at the beginning of step 781, hence before any further operations of step 781 are performed ("debounce delay"). For example, the debounce delay 'B' may be in the range from 0.02 s to 0.5 s. The debounce delay allows the hardware of the drug delivery device 1 to settle before the new (final) ECR is taken in step 781.

Step 781 comprises taking an ECR, for example using the rotary sensor system 129. In particular, the electronic control unit 110, specifically the main microcontroller 111, may operate the sensor arrangement 120 to provide new Gray Code data.

After step 781, the operation proceeds to step 782 ("Is GCC Dummy Value"). Step 781 includes checking whether the stored GCC is the Dummy Value. If 'yes', the operation proceeds to step 783 ("Store (final) ECR as GCC"). In step 783, the (final) ECR, which was taken in step 781, is stored as the GCC. For example, the electronic control unit 110 may be configured to write the (final) ECR as GCC in the memory unit 112. Thereafter, the operation proceeds to step 490 ("Exit failure detection functionality").

If the check in step 782 reveals that the GCC is not the Dummy value, the operation proceeds from step 782 to step 783 ("Is (final) ECR different to GCC by 2 counts?").

Step 783 includes comparing whether the (final) ECR is different from the stored GCC by (at least) a (first) certain extent. In case of the exemplary embodiment presented above, step 783 includes checking whether the (final) ECR is different from the GCC by 2 counts (as in step 680 of method 600). In other embodiments, step 783 may include checking whether the (final) ECR differs from the GCC
- by another predetermined value,
- by any one of a plurality of predetermined values,
- by at least a predetermined value, or
- by more than a predetermined value.

However, in this exemplary embodiment, the first certain extent, the second extent, and the third certain extent are all the same, namely 2 counts.

If the result in step 783 is 'yes', the operation proceeds to step 470 ("Detect rotary switch failure") explained above with regard to FIG. 4.

If the result in step 783 is 'no', the operation proceeds to step 490 ("Exit failure detection functionality").

Step sequence 780 is only performed once at the maximum for each time the electronic system 100, 100A is switched to the failure detection functionality. In more detail, step sequence 780 is only started if the axial switch 220 is released in the monitoring loop of the failure detection functionality before time 'D' has passed.

Turing back to step 740, in addition to step 640, step 740 may comprise checking whether (at least) a time 'E' has passed. This may include comparing a current point of time with the stored (second) point of time. Alternatively or additionally, this may include whether a current value of the (second) time is the same or exceeds time 'E'.

If it is determined in step 740 that time 'E' has not passed, the operation starts step 740 again. There might be a waiting step (not shown) before step 740 is started again. The waiting step may include waiting for the predetermined time interval 'J'. The waiting state helps to save electrical power.

If it is determined in step 740 that time 'E' has passed, the operation proceeds to step 745 ("Set PER equal to ECR. Take new ECR. If PER is Dummy Value, set it to new ECR reading. Reset timer for 'E'.").

In other words, once step 740 has been entered, step 740 may be repeated until:

- The rotary switch 230 indicates rotation of the first member 20 relative to the button module 11; method 700 ends and the electronic system 100 enters the measurement state.
- The axial switch 220 is released (i.e. no longer in its activating state); in this case, the operation proceeds to step sequence 780.
- The time 'D' has passed since last switching from the first mode to the failure detection functionality; in this case the operation proceeds to step 645 and further to step 490.
- The time 'E' has passed (since the stored (second) point in time and/or since the (second) timer has been started); in this case the operation proceeds to step 745.

Step 745 ("Set PER equal to ECR. Take new ECR. If PER is Dummy Value, set it to new ECR reading. Reset timer for 'E'") comprises setting the PER to ECR and taking a new ECR. In other words, the present ECR is stored as the new PER. The sensor arrangement 120 of rotary sensor system 129 is operated (for example by the electronic control unit 110, preferably by the main microcontroller 111) to obtain new Gray code data which is stored as the new ECR.

If the present PCR corresponds to the Dummy value, the PER may be set to the new ECR. In other words, the new ECR may be stored as the new PER.

Step 745 may further include resetting the (second) timer for time 'E' (i.e. starting the second timer again) and/or storing the current point in time as the new (second) point in time.

After step 745, the operation proceeds to step 750 again. By this, the monitoring loop is closed in method 700.

In this embodiment, step 745 is performed with a sampling rate 1/'E' in the failure detection functionality, in more detail in the monitoring loop comprising steps 710, 750, 751, 740, and 745. In other words, the sensor arrangement 120 is operated with this sampling rate in order to take the new ECR, respectively. As noted above, the sampling rate is preferably in the range from 0.2 Hz to 5 Hz, for example 1 Hz. Accordingly, the time (interval) 'E' is preferably in the range from 0.2 s to 5 s, for example 1 s.

Accordingly method 700 comprises checking whether the measurement data obtained from the sensor arrangement 120 indicates that an extent of rotational movement of the first member 20 relative to the button module 11 corresponds to the (second) certain extent in step 750 and/or the (third) certain extent of step 751 with said sampling rate.

Method 700 exhibits more reliable detection of failures of the rotary switch 230. This is explained in the following.

At least if the first member 20 rotates relative to the button module 11 by a multiple of 360°, the relative rotational position in step 680 of method 600 (and similarly in step sequence 780 of method 700) is the same as at step 401. Accordingly, the (final) ECR and the GCC may be identical. Hence, the comparison of the (final) ECR to the GCC in step 680 cannot indicate the relative rotation, respectively. Therefore, failure of the rotary switch 230 is not detected in such cases by method 600.

Operating the sensor arrangement 120 also periodically within the monitoring loop as in method 700 reduces the risk that actual relative rotational movement between the first member 20 and the button module 11 is not detected by using the rotary sensor system 129.

The repeated comparison of the ECR to both the PER (in step 750) and the GCC (in step 751) exhibits enhanced reliability of detection of failure of the rotary switch 230. It is less likely that, on the one hand, both the PER and GCC relate to relative rotational positions different from a relative rotational position in which the new ECR is taken and, on the other hand, both the PER and GCC are identical to the new ECR. As it is evident from above, depending on the embodiment of the rotary sensor system 129, different relative rotational positions may lead to identical Gray code data.

Operating the sensor arrangement 120 in the failure detection functionality more than once as in method 700 improves the detection reliability. In particular, failure detection is also possible in cases where the GCC corresponds to the Dummy Value.

Therefore, the electronic control unit 120 is preferably configured to operate the sensor arrangement 120 at least twice in the failure detection functionality.

On the other hand, the operation according to method 600 reduces the consumption of electrical power compared to the operation according to method 700.

Figure 8:
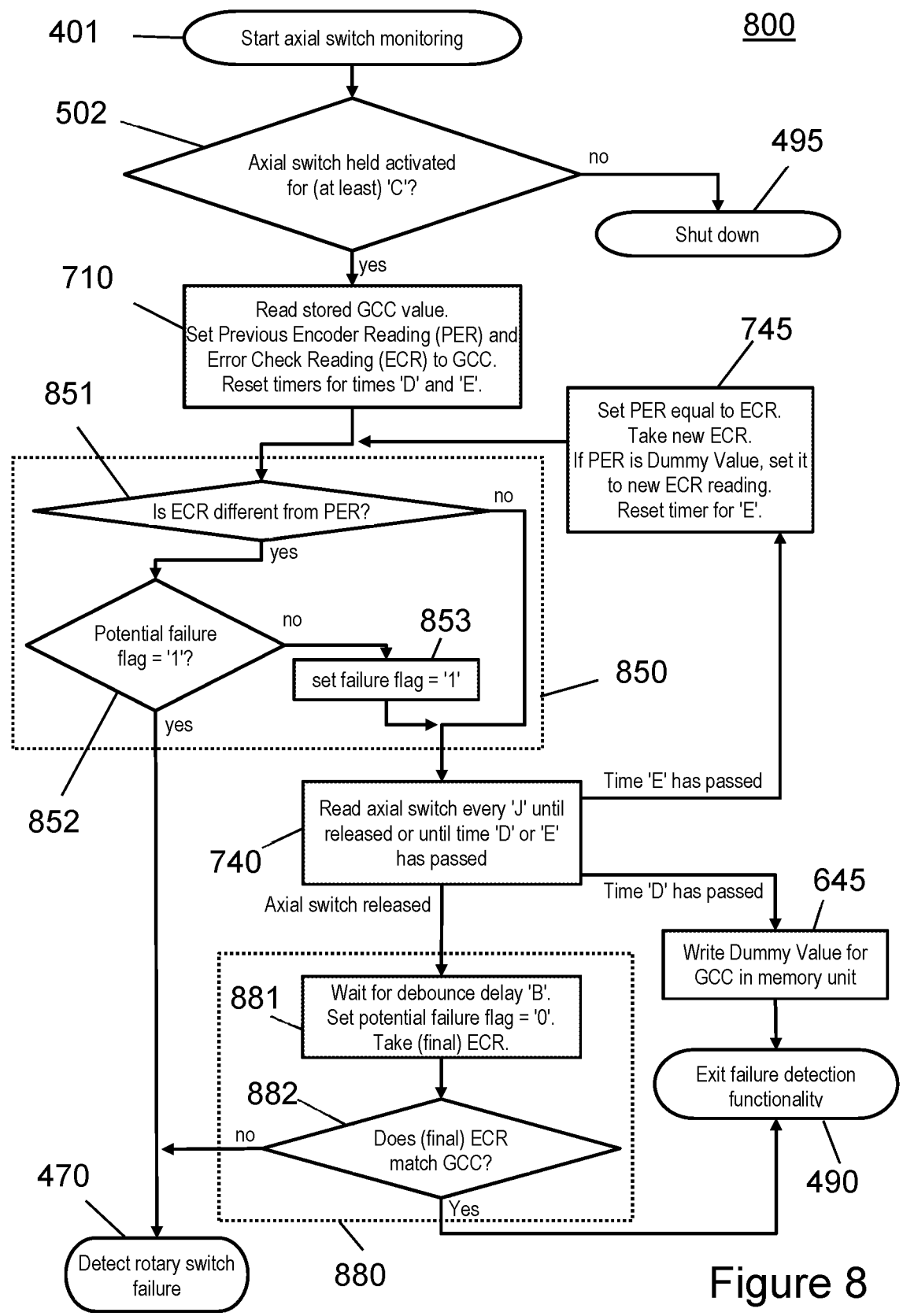
FIG. 8 shows a fifth method for operating the electronic systems of FIG. 2 and FIG. 3.

Regarding method 800 shown in FIG. 8, only the differences to method 700 are described in detail. Apart from that, method 800 corresponds to method 700 (and to methods 400 to 600 as well, if applicable). The same modifications and advantages are applicable accordingly.

In method 8, steps 750 and 751 for determining failure or the rotary switch 230 within the monitoring loop are replaced by step sequence 850. Moreover, step sequence 780 for determining failure of the rotary switch 230 after having exit the monitoring loop due to release of the axial switch 220 is replaced by step sequence 880.

Step sequence 850 starts with step 851 ("Is ECR different from PER?").

Step 851 includes comparing whether the ECR is different from the stored PER by (at least) a (second) certain extent. In this embodiment, step 851 includes checking whether the ECR is different from the PER (i.e. different by at least 1 count). In other embodiments, step 851 may include checking whether the ECR differs from the GCC
- by another predetermined value,
- by any one of a plurality of predetermined values,
- by at least a predetermined value, or
- by more than a predetermined value.

If the ECR is different from the PER in terms of step 851, the operation proceeds to step 852 ("Potential failure flag=1?"). Step 852 comprises checking whether a potential failure flag is set, for example whether a value of the potential failure flag is '1' or 'true'. If the failure flag is already set, this indicates that relative rotation between the first member 20 and the button module 11 during the error detection state corresponds now to at least 2 counts. Hence, the operation proceeds to step 470 ("Detect rotary switch failure") and determines failure of the rotary switch 230.

If the check in step 852 reveals that the potential failure flag has not been set yet (i.e. the value of the potential failure flag is '0' or 'false', for example), the operation proceeds to step 853. Step 853 includes setting the potential failure flag. If the failure flag has not been set yet, this indicates that the ECR is different from the PER for the first time in the current monitoring loop.

Step 851 may include to proceed directly to step 740 in case that PER corresponds to the Dummy Value.

As explained above, a certain angle of relative rotation between the first member 20 and the button module 11 might occur without triggering the rotary switch 230 due to mechanical variations and/or tolerances. Step sequence 850 includes a similar approach than step 750 in method 700 for preventing incorrect determination of failure of the rotary switch 230 due to such harmless relative rotations.

If it is determined in step 740 that that the axial switch 220 is released (before time 'D' has passed since the activation of the failure detection functionality), operation proceeds from step 740 to step sequence 880.

Step sequence 880 starts with step 881 ("Wait for debounce delay 'B'. Set potential failure flag='0'. Take (final) ECR"). Step 881 comprises removing the potential failure flag, for example by setting the value for the potential failure flag back to '0' or 'false', and taking the final ECR.

Step 881 further includes waiting for the debounce delay and then taking the (final) ECR using the rotary sensor system. In particular, the electronic control unit 110, preferably specifically the main microcontroller 111, may operate the sensor arrangement 120 to provide new Gray Code data like in step 680.

Then, operation proceeds to step 882 ("Does (final) ECR match GCC?"). Step 882 includes comparing whether the (final) ECR is different from the stored GCC by (at least) a (first) certain extent. In this embodiment, step 882 includes checking whether the (final) ECR is different from the GCC by at least 1 count. In other embodiments, step 882 may include checking whether the (final) ECR differs from the GCC
- by another predetermined value,
- by any one of a plurality of predetermined values,
- by at least a predetermined value, or
- by more than a predetermined value.

It is noted that the relative rotation arising from the mechanical variations and/or tolerances typically are related to displacements against restoring forces in the dose setting and drive mechanism 300 while the dose button 11 is pressed. After the dose button 11 is released (and hence after axial switch 220 is switched back to its idle state, such displacements and the corresponding (harmless) relative rotation is reversed. Hence, the (final) check for relative rotation in step 882 can be stricter than the check for relative in step sequence 850.

If the check in step 882 exhibits that the current position (which is indicated by the final ECR) differs from the GCC, the operation proceeds to step 470 and determines failure of the rotary switch 230. Otherwise, operation proceeds to step 490 ("Exit failure detection functionality") as in method 700.

FIG. 9 shows the button module 11 for the injection device 1 of FIG. 1 with the electronic system 100, 100A according to the present disclosure. The button module 11 comprises a module outer 50, a cover 51, and a chassis lower 52. The cover 51 covers a proximal end of module outer 50. The module outer 50 and the cover 51 enclose an interior of the button module 11. The module outer 50 surrounds an upper part of the chassis lower 52. The module outer 50 and the chassis lower 52 may be rotationally and/or axially fixed together. In a modification, the module outer 50 and the chassis lower 52 are formed integrally (as one single part).

In this embodiment, a circuit board assembly 115, a battery constituting the electrical power supply 150, the axial switch 220, the rotary switch 230, and the sensor arrangement 120 are mounted in the interior of the button module 11.

The button module 11 is based on the embodiment described in EP 20315451.3. For example, the axial switch 220 and the rotary switch 230 are implemented accordingly.

The circuit board assembly 115 includes the electronic control unit 110 and the communication unit 140. The electronic control unit 110 and the communication unit 140 are not shown in FIG. 9.

The button module 11 is mounted to the dose setting and drive mechanism 300 (not completely shown in FIG. 9) such that the button module 11 is positioned at a proximal end of the dial sleeve 302 of the dose setting and drive mechanism 300.

Limited axial travel of the button module 11 relative to the dial sleeve 302 is allowed. Near to its proximal end, the dial sleeve 302 comprises clutch teeth (not shown) located on its inner diameter. The clutch teeth of the dial sleeve 302 are for engaging a clutch component when the button module 11 in the initial relative position relative to the dial sleeve 302. The button module 11 is rotationally and axially fixed to the clutch component. For example, the button module 11 may be clipped to the clutch component during assembly in order to fix the button module 11 rotationally and axially to the clutch component. The clutch component may be a member of the dose setting and drive mechanism 300 that is different from the first member 20.

FIG. 9 shows the button module 11 in a depressed position (i.e. the activating relative position). In other words, the button module 11 in the distal direction towards the dial sleeve 302 against the restoring force of the clutch spring (not shown) by the user. In the depressed position, the clutch teeth of the dial sleeve 302 are disengaged from the clutch component. By this, the clutch component and the button module 11 are rotationally de-coupled from the dial sleeve 302.

In this depressed position, the button module 11 can rotate relative to the dial sleeve 302. In the depressed position, axial switch 220 is depressed and contacts of the axial switch 220 abut corresponding contact areas at an underside (distal side) of the circuit board assembly 115 (see EP 20315451.3 for more details).

During dose delivery operation, the button module 11 is in the depressed position and the dose dial sleeve 302 rotates relative to the button module 11. The rotary switch 230 is actuated by teeth 303 that are provided directly at the proximal end of the dial sleeve 302. As a consequence, the rotary switch 230 provides the second signal to the electronic control unit 110 (in case there is no failure of the rotary switch 230). This indicates that dose delivery operation is in progress.

The encoder component 125 (in this embodiment the encoder ring) is fixed to the proximal end of the dial sleeve 302 and comprises the angularly separated detection regions 126 at an outer circumferential surface. The encoder component 125 further comprises non-detection regions 127 on its outer circumferential surface between adjacent detection regions 126. Accordingly, the non-detection regions 127 are angularly separated as well. The detection regions 126 comprise a higher reflectance than the non-detection regions 127.

FIG. 9 schematically shows the two optoelectronic sensors 122A and 122B. A first IR radiation emitter 121A is arranged adjacent to the first sensor 122A and a second IR radiation emitter 121B is arranged adjacent to the second sensor 122B.

The electronic control unit 110 of the circuit board assembly 115 can operate the radiation emitters 121A, 121B and the sensors 122A, 122B to provide measurement data regarding the relative rotational position of the encoder component 125 and hence of the number sleeve 301 relative to the button module 11. Dependent on said relative rotational position, the sensors 122A, 122B together generate Gray code output data as described above. For example, the Gray code data '10' may be generated by the sensor arrangement in case the first radiation emitter 121A and the first sensor 121 face one of the detection regions 126 whereas the second radiation emitter 121B and the second sensor 122 face one of the non-detection regions 127.

Figure 10:
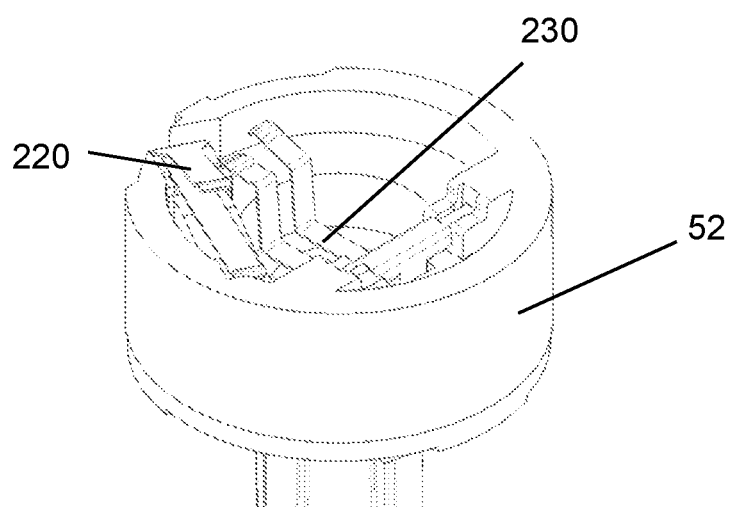
FIG. 10 shows an axial switch and a rotary switch of the button module of FIG. 9 in an interior of the button module.

FIG. 10 shows a perspective view of the axial switch 220 and the rotary switch 230 of the electronic system 100, 100A in the interior of the button module 11 of FIG. 9. These embodiments of the axial switch 220 and the rotary switch 230 are described in EP 20315451.3 in more detail.

REFERENCE NUMERALS

1 injection device (drug delivery device)
10 housing
11 button module (second member)
12 dial grip
13 dosage window
14 container/container receptacle
15 needle
16 inner needle cap
17 outer needle cap
18 cap
20 first member
50 module outer
51 cover
52 chassis lower
100, 100A electronic system
110 electronic control unit
111 main microcontroller
112 memory unit
113 sensor controller
114 clock unit
115 circuit board assembly
120 sensor arrangement
121A, 121B radiation emitter
122A, 122B sensor
125 encoder component
126 detection region
127 non-detection region
129 rotary sensor system
140 communication unit
150 electrical power supply
220 first switch (axial switch)
230 second switch (rotary switch)
300 dose setting and drive mechanism
301 number sleeve
302 dial sleeve
303 teeth

The invention claimed is:

1. An electronic system for a drug delivery device, the drug delivery device comprising a dose setting and drive mechanism, which is configured to perform a dose setting operation for setting a dose to be delivered by the drug delivery device and a dose delivery operation for delivering the set dose, the dose setting and drive mechanism comprising a first member that moves relative to a second member during the dose delivery operation, the electronic system comprising:
   a first switch configured to be activated by a user operation that occurs in conjunction with the dose delivery operation;
   a second switch configured to indicate the movement of the first member relative to the second member during the dose delivery operation;
   a sensor arrangement, the sensor arrangement being operable to provide position data that can be used to distinguish between different positions of the first member relative to the second member; and
   an electronic control unit configured to control operation of the electronic system, wherein the electronic control unit is electrically connected to the first switch, the second switch, and the sensor arrangement, and wherein the electronic control unit is configured to:
      activate a failure detection functionality for detecting failure of the second switch if the first switch is held activated whereas the second switch does not indicate the movement of the first member relative to the second member;
      operate, in the failure detection functionality, the sensor arrangement; and
      determine failure of the second switch based on the position data obtained from the sensor arrangement.

2. The electronic system according to claim 1, wherein the electronic system comprises a communication unit for communication with a second device, wherein the electronic control unit is configured to switch the electronic system to a pairing state for establishing a data connection to the second device for allowing a transfer of data from the electronic system to the second device and/or from the second device to the electronic system if the first switch is held activated for at least a predetermined time and then released.

3. The electronic system according to claim 1, wherein the first member rotates relative to the second member during the dose delivery operation, wherein the first switch comprises an axial switch, a foil switch, and/or a touch sensor, and the second switch is a rotary switch configured to indicate rotation of the first member relative to the second member.

4. The electronic system according to claim 1, wherein the electronic system is configured to determine, with the failure detection functionality, failure of the second switch if the position data obtained from the sensor arrangement with the failure detection functionality indicates that an extent of the movement of the first member relative to the second member is equal to a predetermined extent of movement, is greater than the predetermined extent of movement, or is greater than or equal to the predetermined extent of movement.

5. The electronic system according to claim 1, wherein the dose setting and drive mechanism is configured such that the movement of the first member relative to the second member during dose delivery operation corresponds to a dose delivered during dose delivery operation, wherein the electronic control unit is configured to:

switch the electronic system to a measurement state when the second switch indicates the movement;

deactivate the failure detection functionality when switching to the measurement state if the failure detection functionality is active when switching to the measurement state;

not activate the failure detection functionality in the measurement state;

operate the sensor arrangement in the measurement state to provide measurement data describing the movement of the first member relative to the second member; and determine a size of the dose delivered based at least on the measurement data obtained by operating the sensor arrangement in the measurement state.

6. The electronic system according to claim 5, wherein the electronic control unit is configured to operate the sensor arrangement in the measurement state with a measurement accuracy that is higher than a measurement accuracy at which the sensor arrangement is operated for the failure detection functionality, wherein a sampling rate in the measurement state is at least 100 HZ.

7. The electronic system according to claim 5, wherein electronic control unit comprises a main microcontroller and a sensor controller, wherein the main microcontroller operates the sensor arrangement in the failure detection functionality, and the sensor controller operates the sensor arrangement in the measurement state.

8. The electronic system according to claim 5, wherein the electronic control unit is prevented from providing any measurement results regarding doses delivered during dose delivery operations after the electronic control unit has determined failure of the second switch at least once.

9. The electronic system according to claim 1, wherein the electronic control unit is configured to operate, in the failure detection functionality, the sensor arrangement at least when the first switch is released.

10. The electronic system according to claim 1, wherein the electronic system is configured to provide a failure alert if failure of the second switch is determined.

11. The electronic system according to claim 1, wherein the sensor arrangement comprises at least one of a light source with a corresponding optical sensor, an electrical sliding contact sensor, a mechanical switching arrangement, an inductive sensor, or a magnetic sensor.

12. The electronic system according to claim 1, wherein the electronic system comprises a memory unit and is configured to store the position data obtained from the sensor arrangement.

13. A button module for a drug delivery device, the drug delivery device comprising a dose setting and drive mechanism, which is configured to perform a dose setting operation for setting a dose to be delivered by the drug delivery device and a dose delivery operation for delivering the set dose, the dose setting and drive mechanism comprising a first member, wherein the button module is permanently mounted or releasably mountable to the dose setting and drive mechanism such that the first member moves relative to the button module during the dose delivery operation, wherein the button module comprises an electronic system comprising:

a first switch configured to be activated by a user operation that occurs in conjunction with the dose delivery operation;

a second switch configured to indicate the movement of the first member relative to the button module during the dose delivery operation;

a sensor arrangement the sensor arrangement being operable to provide position data that can be used to distinguish between different positions of the first member relative to the button module; and an electronic control unit configured to control operation of the electronic system, wherein the electronic control unit is electrically connected to the first switch, the second switch, and the sensor arrangement, and wherein the electronic control unit is configured to:

activate a failure detection functionality for detecting failure of the second switch if the first switch is held activated whereas the second switch does not indicate the movement of the first member relative to the button module;

operate, in the failure detection functionality, the sensor arrangement; and determine failure of the second switch based on the position data obtained from the sensor arrangement.

14. The button module according to claim 13, wherein the electronic system comprises a communication unit for communication with a second device, wherein the electronic control unit is configured to switch the electronic system to a pairing state for establishing a data connection to the second device for allowing a transfer of data from the electronic system to the second device and/or from the second device to the electronic system if the first switch is held activated for at least a predetermined time and then released.

15. The button module according to claim 13, wherein the first member rotates relative to the button module during the dose delivery operation, wherein the first switch comprises an axial switch, a foil switch, and/or a touch sensor, and the second switch is a rotary switch configured to indicate rotation of the first member relative to the button module.

16. The button module according to claim 13, wherein the electronic system is configured to determine, with the failure detection functionality, failure of the second switch if the position data obtained from the sensor arrangement with the failure detection functionality indicates that an extent of the movement of the first member relative to the button module is greater than or equal to a predetermined extent of movement.

17. The button module according to claim 13, wherein the dose setting and drive mechanism is configured such that the movement of the first member relative to the button module during dose delivery operation corresponds to a dose delivered during dose delivery operation, wherein the electronic control unit is configured to:

switch the electronic system to a measurement state when the second switch indicates the movement;

deactivate the failure detection functionality when switching to the measurement state if the failure detection functionality is active when switching to the measurement state;

not activate the failure detection functionality in the measurement state;

operate the sensor arrangement in the measurement state to provide measurement data describing the movement of the first member relative to the button module; and determine a size of the dose delivered based at least on the measurement data obtained by operating the sensor arrangement in the measurement state.

18. A drug delivery device comprising:

a dose setting and drive mechanism configured to perform a dose setting operation for setting a dose to be delivered by the drug delivery device and a dose delivery operation for delivering the set dose, the dose setting and drive mechanism comprising a first member that moves relative to a second member during the dose delivery operation;

a container receptacle that is permanently or releasably connected to the dose setting and drive mechanism and that is adapted to receive a container containing a medicament; and an electronic system comprising:

a first switch configured to be activated by a user operation that occurs in conjunction with the dose delivery operation;

a second switch configured to indicate the movement of the first member relative to the second member during the dose delivery operation;

a sensor arrangement, the sensor arrangement being operable to provide position data that can be used to distinguish between different positions of the first member relative to the second member; and an electronic control unit configured to control operation of the electronic system, wherein the electronic control unit is electrically connected to the first switch, the second switch, and the sensor arrangement, and wherein the electronic control unit is configured to:

activate a failure detection functionality for detecting failure of the second switch if the first switch is held activated whereas the second switch does not indicate the movement of the first member relative to the second member;

operate, in the failure detection functionality, the sensor arrangement; and determine failure of the second switch based on the position data obtained from the sensor arrangement.

19. The drug delivery device according to claim 18, wherein the second member is a button module that is permanently mounted or releasably mountable to the dose setting and drive mechanism.

20. The drug delivery device according to claim 18, wherein the first member rotates relative to the second member during the dose delivery operation, wherein the first switch comprises an axial switch, a foil switch, and/or a touch sensor, and the second switch is a rotary switch configured to indicate rotation of the first member relative to the second member.

* * * * *